United States Patent
Ye et al.

(10) Patent No.: US 11,402,370 B2
(45) Date of Patent: Aug. 2, 2022

(54) ALARMING METHOD FOR PLATELET AGGREGATION SAMPLE, BLOOD CELL ANALYZER AND STORAGE MEDIUM

(71) Applicant: SHENZHEN MINDRAY BIO-MEDICAL ELECTRONICS CO., LTD., Shenzhen (CN)

(72) Inventors: Bo Ye, Shenzhen (CN); Wenbo Zheng, Shenzhen (CN); Huan Qi, Shenzhen (CN); Xuerong Li, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 279 days.

(21) Appl. No.: 16/809,520

(22) Filed: Mar. 4, 2020

(65) Prior Publication Data
US 2020/0209218 A1    Jul. 2, 2020

Related U.S. Application Data

(63) Continuation of application No. PCT/CN2017/100611, filed on Sep. 5, 2017.

(51) Int. Cl.
| | | |
|---|---|---|
| *G01N 33/49* | (2006.01) | |
| *G01N 15/10* | (2006.01) | |
| G01N 21/64 | (2006.01) | |
| G01N 27/02 | (2006.01) | |
| G01N 15/00 | (2006.01) | |
| G01N 21/47 | (2006.01) | |

(52) U.S. Cl.
CPC ..... *G01N 33/4905* (2013.01); *G01N 15/1012* (2013.01); *G01N 21/64* (2013.01); *G01N 27/02* (2013.01); *G01N 2015/0084* (2013.01); *G01N 2021/4707* (2013.01)

(58) Field of Classification Search
CPC .......... G01N 15/1012; G01N 15/1459; G01N 2015/0084; G01N 2021/4707; G01N 21/64; G01N 27/02; G01N 33/49; G01N 33/4905; G01N 33/4915; G01N 33/86
USPC .............. 436/63, 69, 150, 164, 172; 422/73, 422/82.01, 82.02, 82.05, 82.08
See application file for complete search history.

(56) References Cited

U.S. PATENT DOCUMENTS

| | | | |
|---|---|---|---|
| 5,656,442 A | 8/1997 | Ginsberg | |
| 5,891,734 A * | 4/1999 | Gill | G01N 35/109 436/805 |
| 6,025,201 A | 2/2000 | Zelmanovic et al. | |
| 7,595,169 B2 * | 9/2009 | Swaim | G01N 33/86 435/13 |
| 9,272,280 B2 * | 3/2016 | Viola | B01L 3/5027 |
| 2003/0138871 A1 | 7/2003 | Shine et al. | |
| 2011/0312015 A1 | 12/2011 | Velaskar | |
| 2013/0065317 A1 * | 3/2013 | Fukuma | G01N 15/06 436/63 |
| 2015/0276769 A1 | 10/2015 | Yamaguchi et al. | |
| 2017/0363610 A1 * | 12/2017 | Linssen | G01N 33/49 |
| 2019/0049428 A1 * | 2/2019 | Murata | G01N 33/86 |

FOREIGN PATENT DOCUMENTS

| | | |
|---|---|---|
| CN | 101046439 A | 10/2007 |
| CN | 106383223 A | 2/2017 |
| CN | 206074613 U | 4/2017 |
| CN | 110383037 A | 10/2019 |
| WO | WO 2017141508 A1 | 8/2017 |

OTHER PUBLICATIONS

Analysis of the Platelet Counting Difference Between Optical Method and Electrical Impedance Method and the Alarm Information of Instrument. Published on Laboratory Medicine and Clinic vol. 35, No. (22), Nov. 30, 2014.

* cited by examiner

*Primary Examiner* — Maureen Wallenhorst
(74) *Attorney, Agent, or Firm* — Kory D. Christensen

(57) ABSTRACT

An alarming method for a platelet aggregation sample can include providing a blood sample, preparing a first test sample from the blood sample under a first reaction condition, acquiring a test signal of the first test sample, and obtaining first platelet test data. The method can also include preparing a second test sample from the blood sample under a second reaction condition, acquiring a test signal of the second test sample, and obtaining second platelet test data. The method can further include obtaining an evaluation result based on the first platelet test data and the second platelet test data, determining whether the evaluation result meets a predetermined condition, and alarming that the blood sample may be the platelet aggregation sample if the evaluation result meets the predetermined condition. The second reaction condition may include a reaction condition for reducing the platelet aggregation degree of the blood sample.

21 Claims, 15 Drawing Sheets

ALARMING METHOD FOR PLATELET AGGREGATION SAMPLE, BLOOD CELL ANALYZER AND STORAGE MEDIUM

CROSS-REFERENCE TO RELATED APPLICATIONS

This application is a bypass continuation of Patent Cooperation Treaty Application No. PCT/CN2017/100611, filed on Sep. 5, 2017, the content thereof is hereby incorporated by reference in its entirety.

TECHNICAL FIELD

Certain embodiments of the present disclosure relate to the field of blood cell analysis, in particular to the detection of a platelet aggregation sample among blood samples.

BACKGROUND ART

Blood cell analysis is widely used in medical research and test to obtain information about red blood cells, white blood cells, platelets and other blood cells. Platelets are produced by megakaryocytes in hematopoietic tissue of bone marrow and have the functions of maintaining vascular endothelial integrity, adhesion, aggregation, release, coagulation promotion, clot contraction, etc. Measuring the number of platelets per unit volume of blood during counting platelets is one of the most commonly used screening tests for hemostasis and coagulation tests.

Existing platelet testing methods include a microscopic method and a blood cell analysis method. The microscopic method can easily identify platelets and check counting results, while the blood cell analysis method is the main conventional method for platelet testing at present, which can quickly and massively carry out automatic tests by detecting electrical impedance and/or scattered light and fluorescence signals of blood cells. However, platelet aggregation exists in some blood samples, which may lead to clinical misdiagnosis and even wrong treatment.

It is difficult for the existing blood cell analyzers to identify platelet aggregation. When platelet aggregation occurs, two or more platelets aggregate together forming a cell has little differences from normal large platelets in morphological characteristics. Therefore, when an aggregation of platelets passes through a detection cell, the test signal (whether it is electrical impedance information by the impedance method or scattered light or fluorescence information by the optical method) of the aggregation of platelets is very similar to that of a large platelet and is thus difficult to be distinguished by the blood cell analyzer. Therefore, it is necessary to develop an automatic alarming method for a sample with platelet aggregation.

SUMMARY

Certain embodiments of the present disclosure firstly provide an alarming method for a platelet aggregation sample, which includes the steps of:

providing a blood sample;

preparing a first test sample from the blood sample under a first reaction condition;

acquiring a test signal of the first test sample to obtain first platelet test data;

preparing a second test sample from the blood sample under a second reaction condition;

acquiring a test signal of the second test sample to obtain second platelet test data;

acquiring an evaluation result based on the first platelet test data and the second platelet test data;

determining whether the evaluation result meets a preset condition; and alarming that the blood sample may be a platelet aggregation sample if the evaluation result meets the preset condition;

wherein the first reaction condition is different from the second reaction condition, and the second reaction condition includes a reaction condition for reducing the platelet aggregation degree of the blood sample.

Further, the first reaction condition differs from the second reaction condition by at least one of reaction temperature, mixing intensity, blood processing reagent concentration or blood processing reagent action time.

Optionally, the first reaction condition includes a reaction temperature that is not higher than 30 degrees Celsius.

Optionally, the second reaction condition includes a reaction temperature that is not lower than 35 degrees Celsius.

Optionally, the first reaction condition includes mixing by using bubbles.

Optionally, the second reaction condition includes mixing by using an agitator arm.

Further, the test signal of the first test sample and the test signal of the second test sample are respectively selected from at least one of an electrical impedance signal, a scattered light signal or a fluorescence signal.

Optionally, the test signal of the first test sample includes an electrical impedance signal, and the test signal of the second test sample includes a forward scattered light signal and a fluorescence signal.

Further, the first platelet test data and the second platelet test data are both platelet count values.

Optionally, the alarming method for a platelet aggregation sample further includes the steps of: outputting alarm information to a user interface indicating that the blood sample may be a platelet aggregation sample.

Further, the step of acquiring the evaluation result includes: acquiring an evaluation value based on the first platelet test data and the second platelet test data; and comparing the evaluation value with a preset threshold value.

Optionally, the alarming method for a platelet aggregation sample further includes the steps of: acquiring a platelet aggregation index of the blood sample based on the evaluation value according to a correlation between a set of preset evaluation values and platelet aggregation indexes; and outputting the acquired platelet aggregation index of the blood sample.

Optionally, the acquired platelet aggregation index of the blood sample is output to a user interface.

Optionally, after the step of obtaining the first platelet test data and before the step of preparing the second test sample from the blood sample under the second reaction condition, the alarming method for a platelet aggregation sample further includes the steps of: determining whether the first platelet test data is abnormal or not; and performing the step of preparing the second test sample from the blood sample under the second reaction condition if the first platelet test data is abnormal.

Certain embodiments of the present disclosure also provide a blood cell analyzer, which includes:

a sample processing device for preparing a test sample from a blood sample;

a sample testing device for detecting a test signal of the test sample;

a controller, which includes a control unit, a signal acquisition unit, a classifying and counting unit and an analyzing and alarming unit;

wherein the control unit is configured to control the sample processing device to respectively prepare a first test sample from the blood sample under a first reaction condition and prepare a second test sample from the blood sample under a second reaction condition, wherein the first reaction condition is different from the second reaction condition, and the second reaction condition includes a reaction condition for reducing the platelet aggregation degree of the blood sample;

wherein the signal acquisition unit is configured to respectively acquire a test signal of the first test sample and a test signal of the second test sample detected by the sample testing device;

wherein the classifying and counting unit is configured to obtain first platelet test data according to the test signal of the first test sample, and obtain second platelet test data according to the test signal of the second test sample; and wherein the analyzing and alarming unit is configured to obtain an evaluation result based on the first platelet test data and the second platelet test data and determines whether the evaluation result meets a preset condition; and the analyzing and alarming unit is configured to alarm that the blood sample may be a platelet aggregation sample if the evaluation result meets the preset condition.

Further, the control unit is configured to control the first reaction condition to be different from the second reaction condition by at least one of reaction temperature, mixing intensity, blood processing reagent concentration or blood processing reagent action time.

Further, the sample processing device includes at least one reaction cell and a temperature control assembly for controlling the temperature of the reaction cell, the at least one reaction cell is configured to respectively prepare the first test sample and the second test sample, the temperature control assembly is connected to the control unit, and the control unit is configured to control the reaction temperature included in the first reaction condition to be not higher than 30 degrees Celsius and the reaction temperature included in the second reaction condition to be not lower than 35 degrees Celsius, by controlling the temperature control assembly.

Further, the sample processing device includes a mixing assembly connected to the control unit, the mixing assembly includes a bubble mixing part and an agitator arm mixing part, and the control unit is configured to control the bubble mixing part for mixing during preparing first test sample under the first reaction condition and control the agitator arm mixing part for mixing during preparing second test sample under the second reaction condition.

Further, the sample testing device includes an electrical impedance testing component which includes a micro pore and two electrodes respectively arranged on two sides of the micro pore.

Further, the sample testing device includes an optical testing component which includes a flow chamber, a light source and at least one light detector.

Further, the first platelet test data and the second platelet test data obtained by the classifying and counting unit are both platelet count values.

Further, the blood cell analyzer further includes a user interface configured for receiving an alarm from the analyzing and alarming unit and prompting that the blood sample may be a platelet aggregation sample.

Further, the analyzing and alarming unit is configured to obtain an evaluation value based on the first platelet test data and the second platelet test data and compare the evaluation value with a preset threshold value to obtain the evaluation result.

Further, the analyzing and alarming unit is configured to acquire a platelet aggregation index of the blood sample according to a correlation between a set of preset evaluation values and platelet aggregation indexes and the evaluation value, and output the acquired platelet aggregation index of the blood sample to the user interface.

The present disclosure, in certain embodiments, further provides a nonvolatile computer-readable storage medium, including instructions stored thereon to implement an alarming method for a platelet aggregation sample when executed by a processor, the alarming method for a platelet aggregation sample including the steps of:

preparing a first test sample from the blood sample under a first reaction condition;

acquiring a test signal of the first test sample to obtain first platelet test data;

preparing a second test sample from the blood sample under a second reaction condition;

acquiring a test signal of the second test sample to obtain second platelet test data;

acquiring an evaluation result based on the first platelet test data and the second platelet test data;

determining whether the evaluation result meets a preset condition; and alarming that the blood sample may be a platelet aggregation sample, if the evaluation result meets the preset condition;

wherein the first reaction condition is different from the second reaction condition, and the second reaction condition includes a reaction condition for reducing the platelet aggregation degree in the blood sample.

Compared with the prior art, the alarming method for platelet aggregation, the blood cell analyzer and the storage medium provided by certain embodiments of the present disclosure perform differentiated processing on two test samples prepared from the same blood sample by controlling the reaction conditions for preparing the first test sample and the second test sample, in such a way that the second reaction condition for preparing the second test sample is capable of reducing the platelet aggregation degree of the blood sample, thereby determining whether the blood sample is a platelet aggregation sample by comparing the platelet test data of the two test samples, realizing automatic alarm on the platelet aggregation sample and reducing the workload of personnel for blood tests. Certain embodiments of the present disclosure can screen suspected platelet aggregation samples simply and quickly almost without increasing the complexity and costs of the blood sample testing process and has a very good application prospect.

LIST OF REFERENCE SIGNS

TABLE 1

| | |
|---|---|
| Blood cell analyzer | 1 |
| Sample collecting device | 10 |
| Sample processing device | 30 |
| First sample processing part | 31 |
| Second sample processing part | 33 |
| Reaction cell | 310 |
| Sample injecting unit | 311 |
| Reagent injecting assembly | 313 |
| Temperature control assembly | 315 |
| Mixing assembly | 317 |
| Conveying assembly | 319 |
| Sample testing device | 50 |
| Electrical impedance testing component | 51 |
| Optical testing component | 53 |
| Bus | 60 |
| Controller | 70 |
| Control unit | 73 |
| Signal acquisition unit | 75 |
| Classifying and counting unit | 77 |
| Analyzing and alarming unit | 79 |
| Evaluation unit | 793 |
| Determination unit | 795 |
| Execution unit | 797 |
| Memory | 83 |
| Processor | 85 |
| User interface | 90 |
| Input apparatus | 93 |
| Output apparatus | 95 |

The following detailed description will further explain various example embodiments of the present disclosure with reference to the above drawings.

DETAILED DESCRIPTION OF EMBODIMENTS

Figure 1:
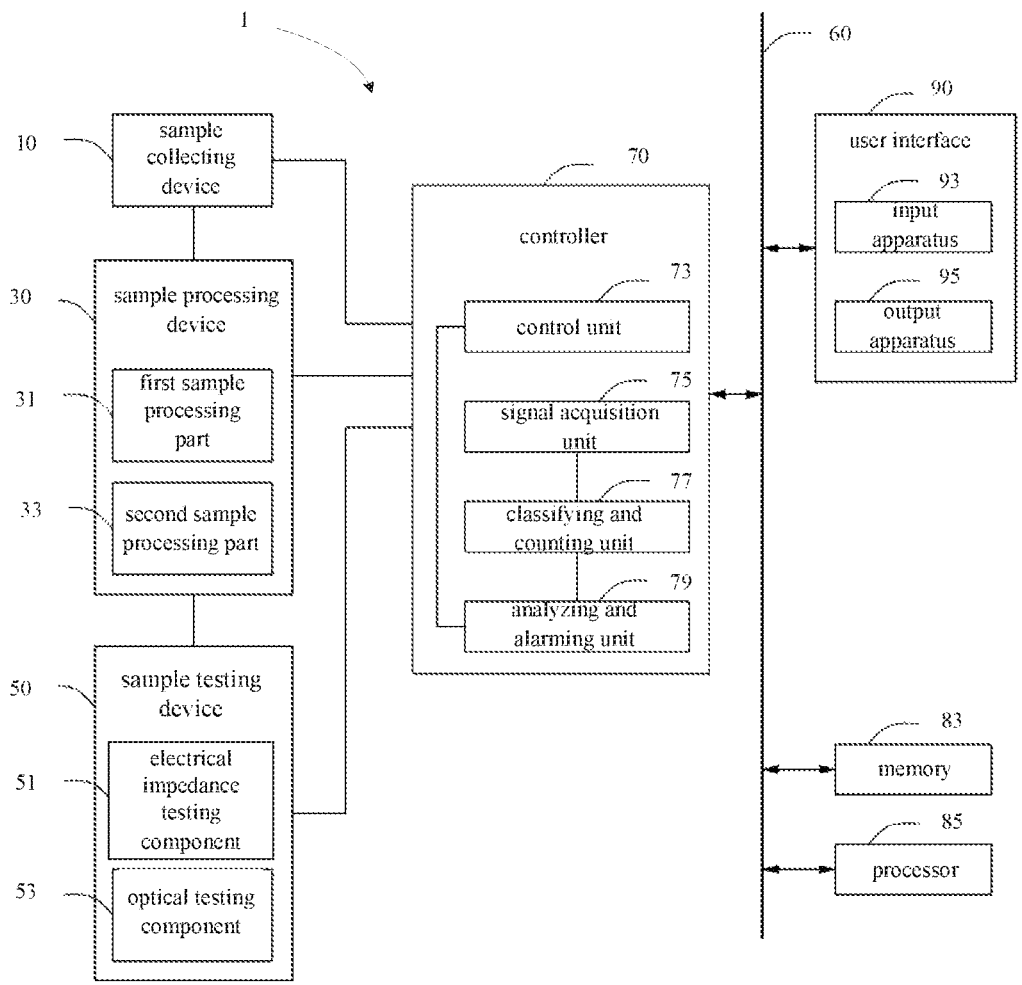
FIG. 1 is a schematic structure diagram of a blood cell analyzer provided in a first embodiment of the present disclosure.

Certain embodiments of the present disclosure firstly provide a blood cell analyzer for analyzing collected blood samples. The analysis includes but is not limited to detection and analysis of blood components such as platelets, red blood cells, white blood cells and hemoglobin. FIG. 1 shows a blood cell analyzer provided in a first embodiment of the present disclosure, and blood cell analyzer 1 comprises a sample collecting device 10, a sample processing device 30, a sample testing device 50, a controller 70, a memory 83, a processor 85 and a user interface 90. The blood cell analyzer 1 has a liquid path system (not shown) for connecting the sample collecting device 10, the sample processing device 30 and the sample testing device 50 for liquid transmission. The controller 70 is directly or indirectly connected in an electrical manner to the sample collecting device 10, the sample processing device 30 and the sample testing device 50 to transmit and exchange data or signals. The controller 70, the memory 83, the processor 85 and the user interface 90 are electrically connected directly or indirectly through a bus 60 to transmit and exchange data or signals.

The sample collecting device 10 is configured to provide a blood sample to the sample processing device 30. In one example, the sample collecting device 10 comprises a sampling needle for drawing a certain amount of blood sample.

The sample processing device 30 is configured for processing a blood sample to prepare a test sample and providing the test sample to the sample testing device 50.

The sample processing device 30 may comprise a plurality of sample processing parts that are capable of respectively preparing different test samples from the blood sample to be tested. In the first embodiment, the sample processing device 30 at least comprises a first sample processing part 31 and a second sample processing part 33. The first sample processing part 31 is configured to prepare a first test sample under a first reaction condition, and the second sample processing part 33 is configured to prepare a second test sample under a second reaction condition. Compared with the first reaction condition, the second reaction condition can reduce the platelet aggregation degree of the blood sample. The method for reducing platelet aggregation degree in the blood sample under the second reaction condition includes but is not limited to increasing reaction temperature, increasing mixing intensity, increasing reaction reagent concentration, prolonging the time for treating the sample with the reagent, etc. The corresponding structure and functional units of the sample processing parts will be described in detail hereinafter. Optionally, the sample processing device 30 may further comprise a sample divider for dividing a blood sample to be tested into a plurality of portions and conveying each portion of the blood sample to a corresponding sample processing part for processing. It can be understood that in other embodiments, the sample processing device 30 may alternatively have only one sample processing part and a cleaning unit in communication therewith to prepare different test samples.

The sample testing device 50 is configured for testing the characteristics of particles in a test sample and acquiring corresponding test signals. The sample testing device 50 comprises at least one sample testing part. In the first embodiment, the sample testing device 50 comprises an electrical impedance testing component 51 and an optical testing component 53. It should be noted that the sample testing device 50 may alternatively have only an electrical impedance testing component or only an optical testing component in other embodiments. Those skilled in the art can understand that the electrical impedance testing component 51 detects the volume of particles in the test sample according to the Coulter principle. When particles with different volumes pass through a micro pore for detection, the internal and external resistances of the micro pore will be changed, and electrical pulses will be generated by a sensor in the micro pore and through a processing circuit. The electrical impedance testing component 51 mainly comprises a micro pore, two electrodes respectively arranged on two sides of the micro pore and a detection circuit connecting the two electrodes. Those skilled in the art can understand that the optical testing component 53 is configured for performing light irradiation on the test sample flowing through a detection area, collecting light (such as scattered light and/or fluorescence) generated by each particle in the test sample due to the light irradiation, and outputting an electrical signal corresponding to the light signal (such as the intensity of the scattered light and/or fluorescence) of each particle. The optical testing component 53 mainly comprises a sheath flow system, a flow chamber, a light source, one or more light detectors and a corresponding detection circuit. Those skilled in the art can understand that the detection target of the sample testing part of the sample testing device 50 is related to the processing method of the blood sample in the sample processing device 30. For example, in one example, the first sample processing part 31 dilutes the blood sample to obtain a first test sample and conveys the first test sample to the electrical impedance testing component 51, and the electrical impedance testing component 51 tests the first sample to obtain an electrical impedance signal; and the second sample processing part 33 performs spheroidization processing and fluorescence staining on the blood sample to obtain a second test sample and conveys the second test sample to the optical testing component 53, and the optical testing component 53 tests the second test sample to obtain scattered light signals and fluorescence signals.

The controller 70 is capable of being configured to control the sample collecting device 10, the sample processing device 30 and the sample testing device 50, acquire a test signal of a test sample from the sample testing device 50, obtain test data of the blood sample based on the test signal, and analyze and process the test data. The controller 70 may be arranged in the blood cell analyzer 1, may be a set of logical relationships embedded in hardware or firmware, or may be a series of programs written in a programming language and stored in the memory 83 or other firmware. The program may be executed by the processor 85 to implement specific functions.

In the first embodiment, the controller 70 comprises a control unit 73, a signal acquisition unit 75, a classifying and counting unit 77, and an analyzing and alarming unit 79 for alarming a platelet aggregation sample.

The control unit 73 is connected to the sample collecting device 10, the sample processing device 30, and the sample testing device 50, so that the sample collecting device 10, the sample processing device 30, and the sample testing device 50 can be controlled to perform tests on blood samples. In the first embodiment, the control unit 73 may control the first sample processing part 31 of the sample processing device 30 to prepare the first test sample under the first reaction condition, and the control unit 73 may control the second sample processing part 33 of the sample processing device 30 to prepare the second test sample under the second reaction condition. The reaction condition includes but is not limited to temperature, mixing intensity, blood processing reagent concentration, time for the blood processing reagent to react with the blood sample, etc., so that the second reaction condition can reduce the platelet aggregation degree in the blood sample compared with the first reaction condition.

The signal acquisition unit 75 is connected to the sample testing device 50, and is configured for performing corresponding amplification and filtering processing on the electrical signal detected by the sample testing device 50, and extracting information related to the volume of particles and/or the characteristics of particle contents in the test blood sample after digitizing the signal. The information includes but is not limited to impedance, scattered light and/or fluorescence signal information of particles in the blood sample. In the first embodiment, the signal acquisition unit 75 acquires information of the first test sample and the second test sample, respectively.

The classifying and counting unit 77 is connected to the signal acquisition unit 75, and is configured to classify and count particles in the blood sample based on information related to the volume of particles and/or characteristics of particle contents in the blood sample, so as to obtain test data of one or more types of blood cells in the blood sample. It can be understood that the classifying and counting unit 77 can generate a one-dimensional histogram, a two-dimensional scatterdiagram or a three-dimensional visualization diagram of the blood sample for classifying and counting according to the information obtained by the signal acquisition unit 75. In one example of the first embodiment, the classifying and counting unit 77 is configured to obtain a platelet count PLT1 of the first test sample and a platelet count PLT2 of the second test sample.

The analyzing and alarming unit 79 is connected to the control unit 73 and the classifying and counting unit 77, and is configured for analyzing the classifying and counting result obtained by the classifying and counting unit 77 to determine whether the blood sample is a platelet aggregation sample. If the determination result is YES, namely the blood sample is a platelet aggregation sample, the analyzing and alarming unit 79 sends an alarming signal to the control unit 73. After receiving the alarming signal, the control unit 73 can control the user interface 90 to prompt the user that the blood sample may be a platelet aggregation sample, and can also control the sample collecting device 10 and/or the sample processing device 30 to retest the same blood sample. When the determination result is NO, namely the blood sample is not a platelet aggregation sample, the analyzing and alarming unit 79 sends an instruction to the control unit 73 to end the workflow, and the control unit 73 controls the sample collecting device 10 to perform testing process on the next blood sample. In one example of the first embodiment, the analyzing and alarming unit 79 obtains an evaluation result based on the platelet count PLT1 of the first test sample and the platelet count PLT2 of the second test sample. The analyzing and alarming unit 79 determines whether the evaluation result meets a preset condition. If the determination result is YES, namely the evaluation result meets the preset condition, an alarm is activated indicating that the blood sample may be a platelet aggregation sample. If the determination result is NO, namely the evaluation result does not meet the preset condition, the workflow ends and a test the next blood sample is continually tested. The alarming method used by the analyzing and alarming unit 79 will be described in detail hereinafter. The memory 83 is configured for storing various types of data, for example, various software programs, such as an operating system and a self-checking program of the blood cell analyzer 1, and data provided and acquired by running these programs. The memory 83 may include random access memory (RAM) and nonvolatile memory such as read-only memory (ROM). The nonvolatile memory may be a hard disk or an internal memory, and the hard disk may include a magnetic hard disk and a solid-state disk (such as flash SSD and PCMSSD).

The processor 85 is configured to execute various software in the memory 83, so as to enable the blood cell analyzer 1 to perform various tests under the control and coordination of the operating system. The processor 85 comprises devices for interpreting computer instructions and processing data in computer software, including but not limited to a central processing unit (CPU), a micro controller unit (MCU), etc.

The user interface 90 is a medium for interaction and information exchange between the blood cell analyzer and a user. In one example, the user interface 90 may be a touch screen capable of recognizing a user's touch operation and presenting test results. In another example, the user interface 90 may comprise an input apparatus 93 and an output apparatus 95. The input apparatus 93 may be a button provided on a housing of the blood cell analyzer or a data input medium electrically connected to the controller 70, such as a keyboard, a mouse and a microphone, etc. The output apparatus 95 may be a display, a printer, a speaker, an indicator light, etc. The controller 70 transmits the test result of the test blood sample to the output apparatus 95, and the output apparatus 95 presents the test result of the test blood sample to the user of the blood cell analyzer.

It can be understood that in one example, the memory 83 of the blood cell analyzer 1 may store a plurality of testing modes, each testing mode including, but not limited to, a condition parameter for preparing a test sample, a test parameter for acquiring test data of the test sample, and parameters and threshold values for analyzing and processing the test data. The user selects a testing mode through the user interface 90 and the corresponding testing mode is executed through the controller 70. Those skilled in the art can understand that the blood cell analyzer 1 may also comprise other structural and functional assemblies, such as communication equipment and data transmission ports, which will not be described in further detail here.

Figure 2:
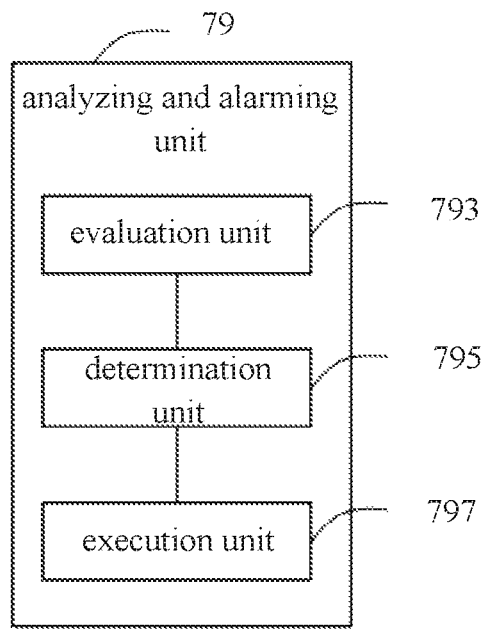
FIG. 2 is a schematic diagram of an analyzing and alarming unit of the blood cell analyzer shown in FIG. 1.

FIG. 2 is a schematic diagram of the analyzing and alarming unit 79 of the blood cell analyzer 1 shown in FIG. 1. Specifically, the analyzing and alarming unit 79 comprises an evaluation unit 793, a determination unit 795, and an execution unit 797.

The evaluation unit 793 is configured to analyze the platelet test data obtained by the classifying and counting unit 77 and obtain an evaluation result. The evaluation includes but is not limited to the steps of comparing the numerical value and/or graphic difference of the platelet test data of the first test sample and the platelet test data of the second test sample, obtaining an evaluation value (EV) by calculating the platelet test data of the first test sample and the platelet test data of the second test sample through a mathematical formula, which reflects the difference therebetween, comparing the evaluation value with a preset threshold value, and obtaining a platelet aggregation index (IN) of the blood sample based on the evaluation value EV. The platelet aggregation index IN is used to qualitatively explain the platelet aggregation degree in a blood sample and will be described in detail hereinafter.

The determination unit 795 is configured to determine whether the blood sample is a platelet aggregation sample. In the first embodiment, the determination unit 795 is configured to determine whether the evaluation result obtained by the evaluation unit 793 meets a preset condition. It is determined that the blood sample may be a platelet aggregation sample if the determination result is YES, and the determination unit 795 sends an instruction to the control unit 73 to end the workflow and to move on to test the next blood sample if the determination result is NO. Specifically, when the evaluation unit 793 obtains a magnitude relationship between the evaluation value EV and a preset threshold value, the preset condition may be that the evaluation value EV should be greater than the preset threshold value. Optionally, the preset condition may alternatively be that the evaluation value EV should be less than the preset threshold value. The design of this preset condition is related to the calculation method of the evaluation value EV, for example, the preset condition is that the evaluation value is less than the preset value when the evaluation value EV is obtained by subtracting the platelet test data of the second test sample from the platelet test data of the first test sample, and the preset condition is that the evaluation value is greater than the preset value when the evaluation value EV is obtained by subtracting the platelet test data of the first test sample from the platelet test data of the second test sample. It can be understood that the preset condition may include a plurality of preset conditions, and the determination result is YES when the plurality of preset conditions are all met.

The execution unit 797 is configured to send the determination result to the control unit 73. Specifically, when the determination result of the determination unit 795 is YES, the execution unit 797 sends an alarming instruction to the control unit 73; and when the determination result of the determination unit 795 is NO, the execution unit 797 sends an instruction to the control unit 73 to end the workflow.

The specific alarming method of the analyzing and alarming unit 79 for a platelet aggregation sample will be further described hereinafter.

Figure 3:
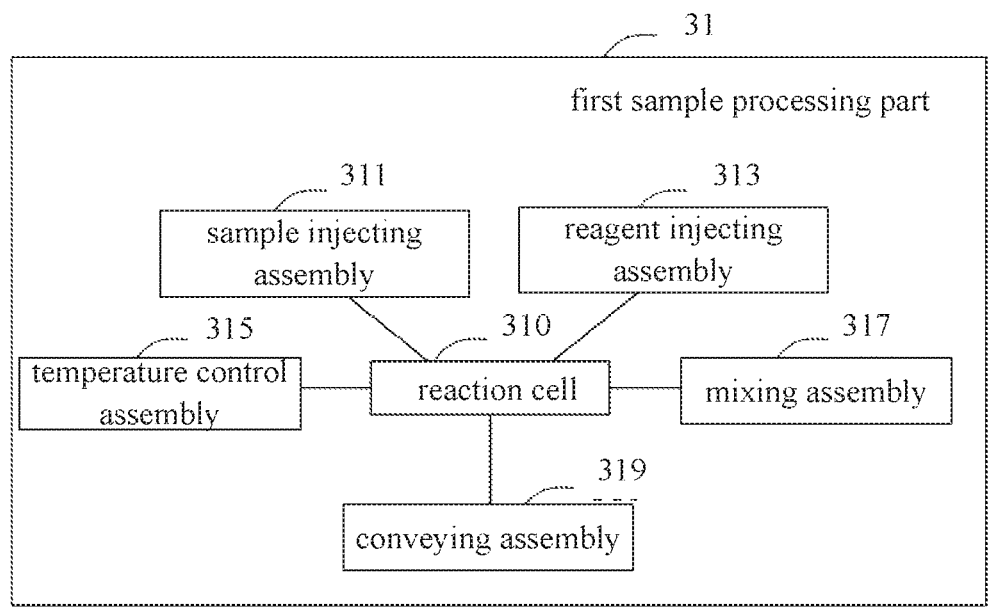
FIG. 3 is a schematic diagram of a first sample processing part of the blood cell analyzer shown in FIG. 1.

FIG. 3 schematically shows an example of a first sample processing part 31 of the blood cell analyzer 1 shown in FIG. 1. In this example, the first sample processing part 31 comprises a reaction cell 310, a sample injecting assembly 311, a reagent injecting assembly 313, a temperature control assembly 315, a mixing assembly 317 and a conveying assembly 319. The reaction cell 310 is configured to provide a place for mixing a blood sample and a blood processing reagent. The sample injecting assembly 311 is configured to provide the blood sample to the reaction cell 310. The reagent injecting assembly 313 is configured to provide the blood processing reagent to the reaction cell 310. The temperature control assembly 315 is configured to control the temperature of the liquid in the reaction cell 310. The mixing assembly 317 is configured to mix the blood sample and the blood processing reagent in the reaction cell 310. The conveying assembly 319 is configured to convey the processed sample to the sample testing device 50.

Those skilled in the art can understand that, the amount of liquid added into the reaction cell 310 by the sample injecting assembly 311 and the reagent injecting assembly 313 can be controlled by the control unit 73 of the controller 70 by setting appropriate elements such as pipelines, valves and dosing pumps.

In this example, the temperature control assembly 315 is capable of receiving a control signal from the control unit 73 and setting and controlling the temperature of the reaction cell 310 based on the corresponding control signal. Optionally, the temperature control assembly 315 may also be configured to control the temperature of the liquid in the sample injecting assembly 311 and/or the reagent injecting assembly 313. The temperature control assembly 315 may comprise a temperature control circuit, a temperature sensor and a heat exchanger. The temperature sensor and the heat exchanger are respectively connected to the temperature control circuit. The temperature sensor is used for sensing the temperature of the reaction cell 310 and outputting a signal related to the sensed temperature. The temperature control circuit controls the heat exchanger to change the temperature in response to the signal output from the temperature sensor. Heat exchange occurs between the heat exchanger and the reaction cell 310.

In this example, the mixing assembly 317 may comprise one or more mixing parts for mixing the blood sample and the blood processing reagent in the reaction cell 310. Those skilled in the art can understand that the mixing assembly 317 can be used to mix the blood sample with a diluent, and the diluted blood sample is delivered to the electrical impedance testing component 51 to detect red blood cells and platelets in the blood sample; the mixing assembly 317 can be used to mix the blood sample with a spheroidizing reagent and a fluorescent dye, and the prepared test sample is delivered to the optical testing component 53 to detect platelets and/or reticulocytes in the blood sample; and the mixing assembly 317 can be used to mix a blood sample with a hemolytic agent and a fluorescent dye, and the prepared test sample is delivered to the optical testing component 53 to detect hemoglobin and/or white blood cells, etc. in the blood sample. The mixing assembly 317 can receive a control signal from the control unit 73, and set and control the operation mode and operation frequency of the mixing part based on the corresponding control signal, thereby controlling the mixing intensity of the blood sample with the blood processing reagent in the reaction cell 310.

In this example, the mixing assembly 317 may comprise a bubble mixing part. Pressure is injected into the reaction cell 310 from a pressure source to generate bubbles, by controlling a switch of an electromagnetic valve via a microcontroller, so as to realize mixing of the blood sample with the blood processing reagent in the reaction cell 310. In one example, the bubble mixing part comprises a bubble control module connected to the microcontroller for controlling the generation speed, quantity and size of bubbles. The mixing assembly 317 may also comprise an agitator arm mixing part, and a motor is controlled by a microcontroller to make an agitator arm extend into the reaction cell 310, so as to mix the liquid through rotation of agitator blades. In one example, the microcontroller is configured to control the rotation speed of the motor through a variable-frequency drive to control the mixing intensity. Optionally, the mixing assembly 317 may comprise the bubble mixing part and the agitator arm mixing part, in which case, based on a corresponding control signal, the mixing assembly 317 is configured to select a mixing part and a corresponding mixing intensity for mixing the blood sample with the blood processing reagent in the reaction cell 310. Those skilled in the art can understand that the mixing intensity of the bubble mixing part is weaker than that of the agitator arm mixing part used in common blood cell analyzers. It can be understood that the mixing assembly 317 can also mix the liquid in the reaction cell 310 in other ways, such as by ultrasound, vortex and vibration.

It can be understood that the blood cell analyzer 1 is capable of controlling the above-mentioned functional units of the first sample processing part 31, so as to prepare required test samples from a blood sample under preset conditions.

It can be understood that the second sample processing part 33 has structures and functions similar to those of the first sample processing part 31 and will not be described in further detail here. In one example of the first embodiment, the first sample processing part 31 of the sample processing device 30 has a mixing part for bubble mixing, and the second sample processing part 33 has a mixing part for mixing with an agitator arm, so that a first test sample and a second test sample can be respectively prepared from a blood sample with different mixing intensities. Limited by the mixing principle, the mixing intensity of the bubble mixing method is usually weaker than that of the agitator arm mixing method. In one example, the blood cell analyzer is provided with a test channel, where a first test sample is prepared by the bubble mixing method, and a platelet test result obtained by the electrical impedance testing component 51 is the first platelet test data; and the blood cell analyzer is further provided with another test channel, where a second test sample is prepared by the agitator arm mixing method, and a platelet test result obtained by the optical testing component 53 is the second platelet test data. The inventors discovered through research that for some samples, the platelet count results obtained by the two test channels are different, and the difference therebetween is well correlated with whether the test blood sample is a platelet aggregation sample. Having tested a large number of clinical samples, the inventors confirmed the existence of the correlation, so that the difference between the platelet test results of the two test channels can be utilized to prompt whether the test blood sample is a platelet aggregation sample.

Various embodiments of the present disclosure will be further described below with reference to an alarming method for a platelet aggregation sample applied to the blood cell analyzer 1 described above.

Figure 4:
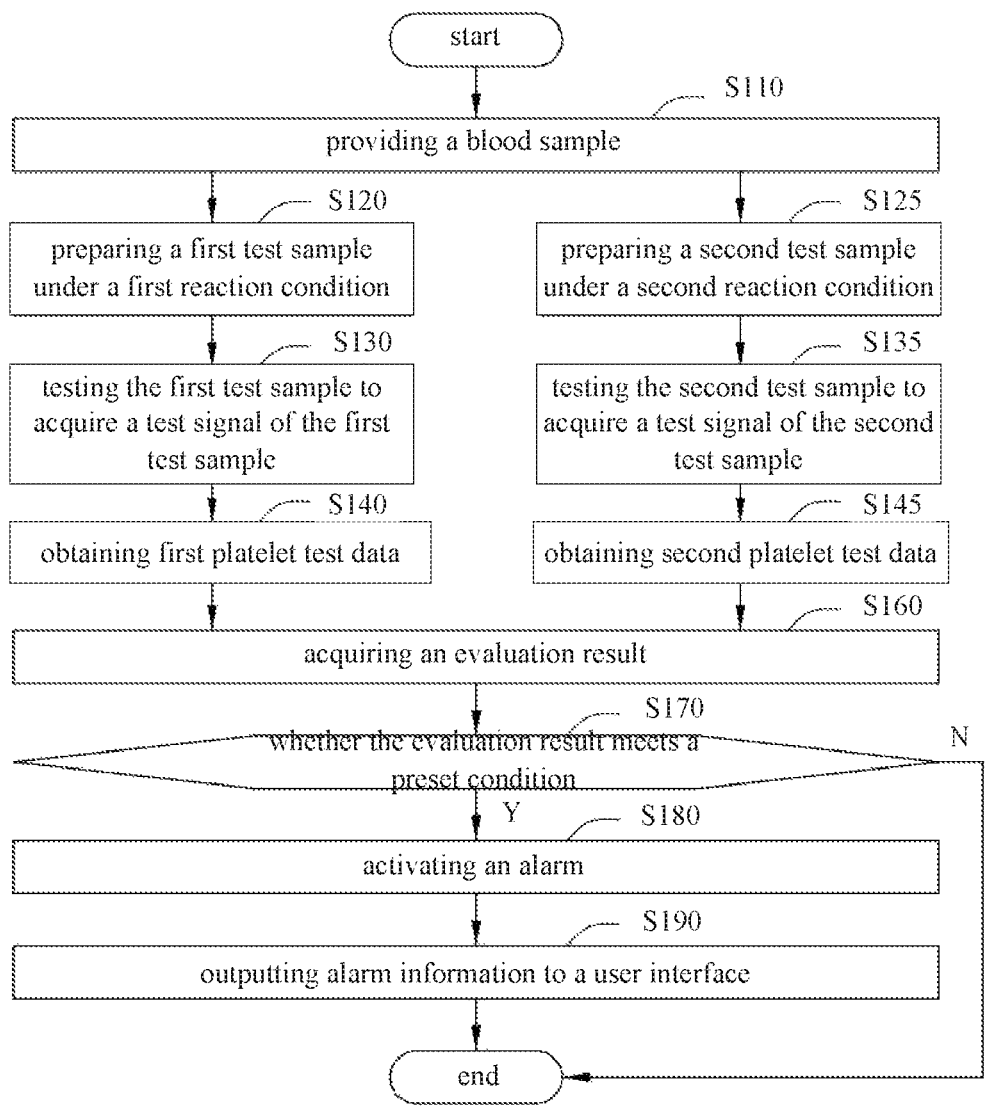
FIG. 4 is a flowchart of an alarming method for a platelet aggregation sample provided in a second embodiment of the present disclosure.

FIG. 4 shows a flowchart of an alarming method for a platelet aggregation sample provided in a second embodiment of the present disclosure, comprising:

step S110, providing a blood sample;
step S120, preparing a first test sample from the blood sample under a first reaction condition;
step S130, testing the first test sample to acquire a test signal of the first test sample;
step S140, obtaining first platelet test data according to the test signal of the first test sample;
step S125, preparing a second test sample from the blood sample under a second reaction condition;
step S135, testing the second test sample to acquire a test signal of the second test sample;
step S145, obtaining second platelet test data according to the test signal of the second test sample;
step S160, acquiring an evaluation result based on the first platelet test data and the second platelet test data;
step S170, determining whether the evaluation result meets a preset condition;
step S180, activating an alarm when the determination result of step S170 is YES; and
step S190, outputting alarm information to a user interface.

In step S110, the blood sample to be tested may be acquired by the sample collecting device 10 of the blood cell analyzer 1. In one example, the sample collecting device 10 draws a certain amount of the blood sample through a sampling needle, and then supplies the drawn blood sample to the sample processing device 30 through a liquid path system. Steps S120, S130, S140, S125, S135 and S145 prepare a first test sample and a second test sample respectively from the same blood sample and respectively test the first test sample and the second test sample, so as to respectively acquire test signals of the first test sample and the second test sample, thus obtaining two sets of test data corresponding to the same blood sample. The conditions for preparing the second test sample include a reaction condition for reducing platelet aggregation. Specifically, in the method provided by the present application, the obtained two sets of test data are test data related to platelet information in the blood sample. These steps will be described in detail below.

The blood sample are treated in steps S120 and S125, and the first reaction condition and the second reaction condition described in steps S120 and S125 are different from each other. Compared with the first reaction condition, the second reaction condition can reduce the platelet aggregation degree in the blood sample. The method for reducing platelet aggregation degree in blood sample under the second reaction condition includes but is not limited to increasing reaction temperature, increasing mixing intensity, increasing a reaction reagent concentration, prolonging the time for treating the sample with the reagent, etc. It can be understood that any other method capable of reducing platelet aggregation in a platelet aggregation sample can be used for the alarming method for a platelet aggregation sample disclosed in this embodiment.

The inventors found through theoretical hypothesis and experimental verification that when the temperature for preparing the first test sample is not higher than 30 degrees Celsius and the temperature for preparing the second test sample is not lower than 35 degrees Celsius, the platelet aggregation degree in the second test sample is reduced in the case of a platelet aggregation sample. In one example, the temperature for preparing the first test sample is 25 degrees Celsius and the temperature for preparing the second test sample is 42 degrees Celsius. The inventors also found that when the mixing intensity during preparation of the second test sample is greater than that during preparation of the first test sample, the platelet aggregation degree in the second test sample is reduced in the case of a platelet aggregation sample. In one example, the first test sample is prepared by mixing with a mixing intensity of 600 revolutions per minute (rpm) via an agitator arm, and the second test sample is prepared by mixing with a mixing intensity of 1400 rpm via an agitator arm. In another example, the first test sample is prepared by mixing using bubbles, in a way of an electromagnetic valve controlling a pressure source to inject pressure into the reaction cell for 0.1 seconds at regular intervals of 0.2 seconds and repeatedly for 5 times; and accordingly, the second test sample is prepared by mixing using an agitator arm with a mixing intensity of 600 rpm, agitating for 1 second at regular intervals of 3 seconds, and repeatedly 4 times, so as to obtain the second test sample with reduced platelet aggregation degree compared to the first test sample. In addition, the inventors also found that for a test sample treated with a hemolytic agent, the platelet aggregation degree of the platelet aggregation sample can also be reduced by increasing the concentration of the hemolytic agent when treating the blood sample and/or prolonging the time for treating the blood sample with the hemolytic. The hemolytic agent is used for dissolving red blood cells in a blood sample, and the main components of the hemolytic agent include a surfactant. That is, the first test sample and the second test sample in accordance with the spirit of various embodiments of the present disclosure can also be obtained by controlling the volume or concentration of the hemolytic agent added to the reaction cell in the first and/or second sample processing parts, respectively, or controlling the respective time periods for the first and second sample processing parts to mix the test sample with the hemolytic agent via the control unit 73. Based on the above findings, the first test sample and the second test sample in accordance with the various embodiments of the present disclosure can be respectively prepared by controlling one or more of the above sets of reaction conditions.

Steps S120 and S125 are executed by the sample processing device 30 under the control of the blood cell analyzer 1. Steps S120 and S125 may be performed simultaneously or sequentially in time. Steps S120 and S125 may be executed by two corresponding sample processing parts, respectively, or may be executed separately by one and the same sample processing part. In one example, a blood sample is divided into at least two sub-samples, and the sub-samples are conveyed to the first sample processing part 31 and the second sample processing part 33, respectively, by a liquid path system. The first sample processing part 31 is configured to prepare the first test sample under the first reaction condition, and the second sample processing part 33 is configured to prepare the second test sample under the second reaction condition. In another example, after the sample collecting device 10 has collected a blood sample, the blood sample is conveyed to the first sample processing part 31 for preparing the first test sample under the first reaction condition, and then the sample collecting device 10 collects a same blood sample again and conveys the blood sample to the second sample processing part 33 for preparing the second test sample under the second reaction condition. In yet another example, after the sample collecting device 10 has collected a blood sample, the blood sample is conveyed to the first sample processing part 31 for preparing the first test sample under the first reaction condition, and then the sample collecting device 10 collects a same blood sample again and conveys the blood sample to the first sample processing part 31 for preparing the second test sample under the second reaction condition.

Those skilled in the art can understand that the blood processing reagents added to the blood sample during the preparation of the first test sample and the second test sample may be the same or different, only one blood processing reagent may be added, or several blood processing reagents may be added. In order to realize the platelet aggregation alarming method, those skilled in the art can understand that the method of preparing the test sample and the method of testing the test sample generally correspond to each other so as to provide information about platelets in the blood sample. The platelet information includes but is not limited to information of platelets, small platelets, large platelets, giant platelets, and platelet clumps in a blood sample. The control of the temperature and mixing of the first reaction condition and the second reaction condition may be performed before, after or simultaneously with the addition of the blood processing reagent.

In steps S130 and S135, the cell analyzer controls the sample testing device 50 to detect signals of particles in the first test sample and the second test sample, respectively. The test signal includes but is not limited to one or more of an electrical impedance signal, a conductance signal, a forward scattered light signal, a side scattered light signal, and a fluorescence signal. The sample testing device 50 may acquire the test signals of the first and second samples to be tested, respectively, through different testing parts, or may acquire the test signals of the first and second samples to be tested, respectively, through the same testing part.

In steps S140 and S145, the controller 70 obtains the first platelet test data and the second platelet test data corresponding to the same blood sample respectively based on the test signal of the first test sample and the test signal of the second test sample. The platelet test data includes but is not limited to one or more of platelet count (PLT), mean platelet volume (MPV) and platelet distribution width (PDW). It can be understood that the platelet test data used in this embodiment is any data that can directly or indirectly reflect the change of platelet aggregation degree in the first and second test samples.

In step S160, the evaluation unit 793 of the controller 70 obtains an evaluation result based on the first platelet test data and the second platelet test data. The evaluation result is used to present whether there is a difference between the first platelet test data and the second platelet test data and/or the degree of the difference between the two. The evaluation result includes but is not limited to a numerical magnitude relationship and/or a degree of graphic difference between the first platelet test data and the second platelet test data, and a numerical magnitude relationship between an evaluation value EV based on the first platelet test data and the second platelet test data and a preset threshold value. In one example, the evaluation result is that the second platelet test data is greater than the first platelet test data. In another example, the evaluation result is that the absolute value of the difference between the second platelet test data and the first platelet test data (i.e., the evaluation value EV) is greater than a preset threshold value of 30. In yet another example, the evaluation result is that the quotient of the second platelet test data and the first platelet test data is less than a preset threshold value of 1.3. In still another example, the evaluation result is that the graph of the second platelet test data is similar (or not similar) to the graph of the first platelet test data. It can be understood that the content of the evaluation result may include one or more items of analysis and comparison results, and is not limited to the above examples. Specifically, the evaluation value EV can reflect the degree of difference between the second platelet test data and the first platelet test data. The evaluation value EV can be the degree of change of the second platelet test data relative to the first platelet test data or the degree of change of the first platelet test data relative to the second platelet test data. The method of calculating the evaluation value EV is not limited to the method disclosed herein. Taking as an example the case where the platelet test data is a platelet count, the evaluation value EV may be the difference or quotient between the second platelet count PLT2 and the first platelet count PLT1, or the reciprocal, multiple or index of the difference or quotient. In one example, $EV=a*(PLT2/PLT1)$, where a is a preset coefficient. In another example, $EV=a*(PLT1/PLT2)$, where a is a preset coefficient. In yet another example, $EV=(PLT2-PLT1)^b$, where b is a preset coefficient. The evaluation value EV may also be other values that can reflect the difference between PLT1 and PLT2, for example, $EV=(PLT2-PLT1)/PLT1$, $EV=(PLT2-PLT1)/PLT2$, etc.

In step S170, the determination unit 795 of the controller 70 determines whether the evaluation result obtained in step S160 meets a preset condition, thereby determining whether the blood sample is likely to be a platelet aggregation sample. It can be understood that the content of this preset condition is related to the content of the evaluation result described in step S160. In one example, the evaluation result in step S160 is the numerical magnitude relationship between the first platelet test data and the second platelet test data, and the preset condition may be that the first platelet test data is less than the second platelet test data. In another example, the evaluation result in step S160 is based on the numerical magnitude relationship between the evaluation value $EV=PLT2/PLT1$ of the first platelet count PLT1 and the second platelet count PLT2 and a preset threshold value of 1.3, and the preset condition may be that the evaluation value EV is greater than a preset threshold value of 1.3. In yet another example, the evaluation result in step S160 is the numerical magnitude relationship between a first evaluation value $EV1=a(PLT2-PLT1)$ and a preset threshold value of 50 and the numerical magnitude relationship between a second evaluation value $EV2=PLT2/PLT1$ and a preset threshold value of 1.5, then the preset condition may be that the first evaluation value EV1 is greater than the preset threshold value of 50 and the second evaluation value EV2 is greater than the preset threshold value of 1.5. In still another example, if the evaluation result in step S160 is that the graph of the second platelet test data is similar (or not similar) to the graph of the first platelet test data, the preset condition may be that the graph of the second platelet test data is not similar to the graph of the first platelet test data. It can be understood that the preset condition may include one or more determination conditions. When all the determination conditions are met, the evaluation result meets the preset condition, and the determination result of step S170 is YES, so that the method proceeds to step S180 where the execution unit 797 sends an alarming instruction to the control unit 73. When the evaluation result in step S160 fails to meet all the determination conditions, the evaluation result does not meet the preset condition, and the determination result in step S170 is NO, so that the workflow ends, and the blood cell analyzer 1 moves on to detect the next blood sample.

It should be noted that in some examples of this embodiment, the preset threshold values set in steps S160 and S170 are statistical empirical values, which are derived from the test results of hundreds of normal blood samples and platelet aggregation samples. For example, for a blood sample, the first and second reaction conditions are controlled by a blood cell analyzer to respectively obtain platelet count results PLT1, PLT2 and their evaluation values, and the platelet aggregation degree of the blood sample is examined by artificial microscopy in accordance with international standards, and the evaluation values of PLT1 and PLT2 are correlated with the results (whether or not platelet aggregation samples) obtained by the artificial microscopic examination. Further, hundreds to thousands of blood samples were tested to obtain a large amount of correlation between the evaluation value and the platelet aggregation sample, the numerical value of the preset threshold value for the alarming method for a platelet aggregation sample provided by the present application can be determined through a statistical method. It is to be understood that, in some examples, the preset threshold value can be modified or corrected by the user through the user interface.

It can be understood that in this embodiment, the calculation method of the evaluation value EV described in steps S160 and S170 is associated with the type of platelet test data acquired in steps S140 and S145 and the setting of the preset conditions in step S170. Specifically, when the platelet test data acquired in steps S140 and S145 are the first platelet count PLT1 and the second platelet count PLT2, if the evaluation value EV is set to be calculated as EV=PLT2−PLT1 and EV=PLT2/PLT1, and the evaluation result in step S160 is a numerical magnitude relationship between the evaluation value EV and a preset threshold value, then the preset condition should be that the evaluation value EV is greater than the preset threshold value. On the contrary, if the evaluation value EV is set to be calculated as EV=PLT1−PLT2 and EV=PLT1/PLT2, and the evaluation result in step S160 is a numerical magnitude relationship between the evaluation value EV and a preset threshold value, then the preset condition should be that the evaluation value EV is less than the preset threshold value. Therefore, in order to realize automatic alarming for a suspected platelet aggregation sample, the setting of the preset condition in step S170 depends on steps S140, S145 and S160. Theoretically, for a platelet aggregation sample, since the second test sample is prepared in step S125 under the second reaction condition for reducing the platelet aggregation degree in the blood sample, the platelet aggregation degree in the second test sample is reduced, and the number of platelets in a dispersed state in the second test sample is greater than the number of platelets in a dispersed state in the first test sample, so that the second platelet count should be greater than the first platelet count. Therefore, in the platelet aggregation alarming method provided by certain embodiments of the present disclosure, when the second platelet test data can reflect the increase in the number of platelets relative to the first platelet test data, the blood sample may be a platelet aggregation sample. In step S190, the execution unit 797 of the controller 70 sends an alarm signal to the user interface 90, and the user interface 90 gives an alarm prompting the user of the blood cell analyzer by means of text, sound, light or a pop-up, that the blood sample tested is suspected to be a platelet aggregation sample. Optionally, the controller 70 can also send the alarm signal to another blood cell analyzer or a smearing and staining machine to initiate a retest of the blood sample. In addition, the user interface 90 can also be used to present or print the first platelet test data and the second platelet test data.

Figure 5:
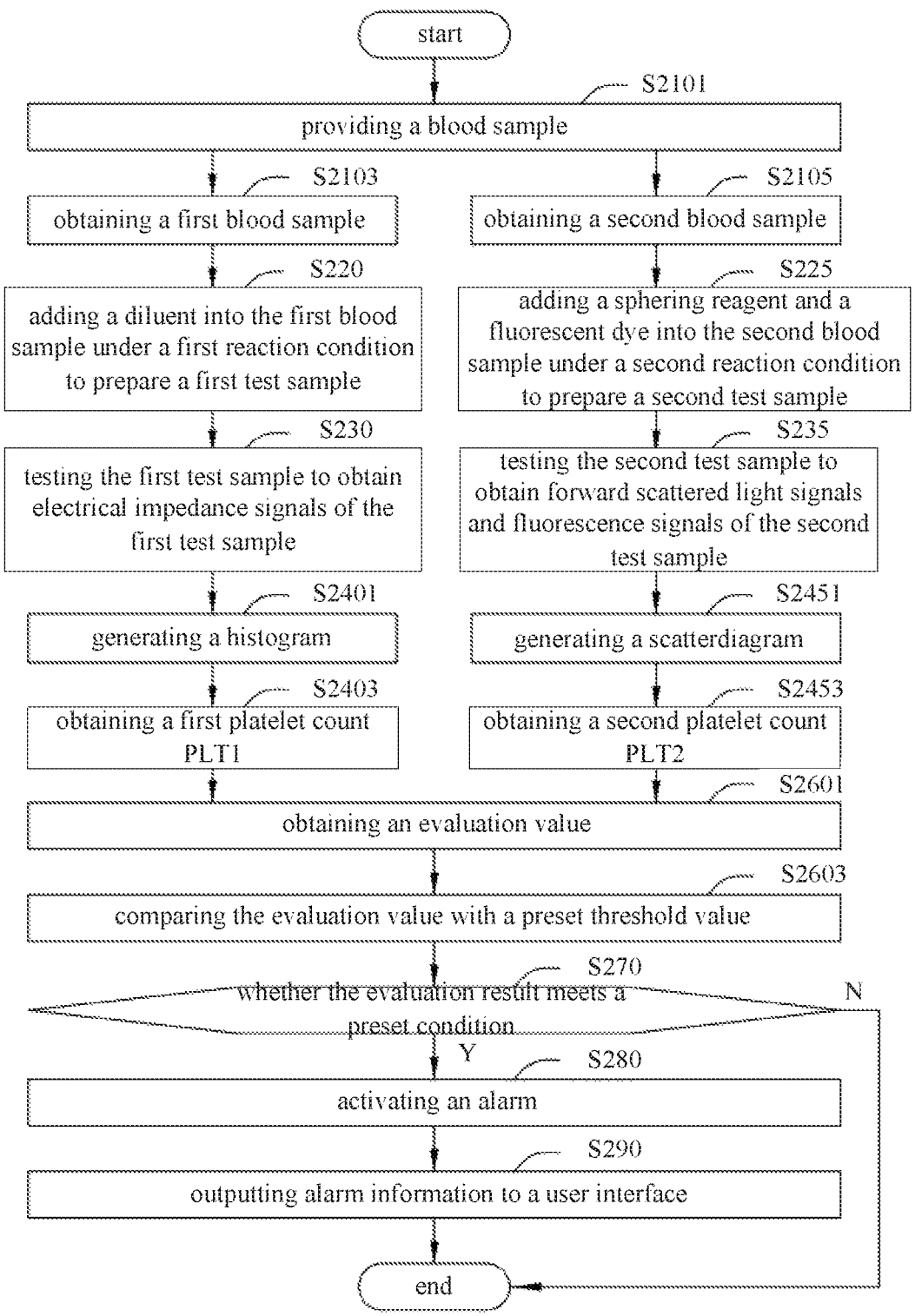
FIG. 5 is an example of the second embodiment shown in FIG. 4.

FIG. 5 shows a flowchart of an example of the alarming method for a platelet aggregation sample provided in the second embodiment above, including the following steps.

In step S2101, a blood sample is provided.

In steps S2103 and S2105, the blood sample is divided into at least two portions, including a first blood sample and a second blood sample. In step S2103, the first blood sample is supplied to the first sample processing part 31. In step S2105, the second blood sample is supplied to the second sample processing part 33.

In step S220, the first sample processing part 31 mixes the first blood sample with a diluent under a first reaction condition to prepare a first test sample. Those skilled in the art can understand that the diluent is used to dilute the blood sample. In step S230, the electrical impedance testing component 51 is used to test the first test sample to obtain electrical impedance signals of the first test sample. In steps S2401 and S2403, the controller 70 generates a volume distribution histogram of cells in the first test sample according to the electrical impedance signal of the first test sample, and obtains the first platelet count PLT1 according to the histogram.

In step S225, the second sample processing part 33 performs spheroidization and fluorescence staining processing on the second blood sample under a second reaction condition to prepare a second test sample. Those skilled in the art can understand that the spheroidization processing refers to the spheroidization of red blood cells in the blood sample by reagents. The fluorescent staining refers to labeling blood cells in the blood sample with dyes. Fluorescent dyes include but are not limited to nucleic acid dyes that can bind to intracellular nucleic acids. For example, the diluent M-68DR of Mindray can be used to spheroidize the blood sample, and the staining solution M-68FR of Mindray can be used to fluorescent stain cells, and the second test sample can be prepared by mixing these reagents with the blood sample. In step S235, the optical testing component 53 is used to test the second test sample to obtain forward scattered light signals and fluorescence signals of the second test sample. In steps S2451 and S2453, the controller 70 generates a two-dimensional scatterdiagram of cells in the second test sample according to the forward scattered light signals and fluorescence signals of the second test sample, and obtains a second platelet count PLT2 according to the scatterdiagram.

Compared with the first reaction condition in step S220, the second reaction condition in step S225 can reduce the platelet aggregation degree in the blood sample, including, but not limited to, increasing the reaction temperature, increasing the mixing intensity, increasing the concentration of the reagent and/or prolonging the time for treating the blood sample with the reagent, which is/are realized by the controller 70 controlling the corresponding sample processing parts respectively. For specific methods, please refer to the foregoing content, which will not be repeated here.

In step S2601, an evaluation value EV is calculated based on PLT1 and PLT2 obtained in the above steps. The calculation method of the evaluation value EV includes but is not limited to EV=f(PLT2−PLT1) and EV=f(PLT2/PLT1). In step S2603, the numerical magnitudes of the evaluation value EV and a preset threshold value are compared with each other to obtain an evaluation result. In step S270, it is determined whether the obtained evaluation result meets a preset condition, for example, whether the evaluation value EV is greater than the preset threshold value. When the determination result is YES, an alarm is activated in step S280, and the alarm information is sent to a user interface in step S290. When the determination result is NO, the workflow ends and the method moves on to test the next blood sample.

It can be understood that in this example, the histogram and the scatterdiagram can be visual graphs or a set of non-visual data, as long as the method described in this example can be implemented.

In this example, the electrical impedance testing component (PLT-I) and the optical testing component (PLT-O) of the blood cell analyzer are used to test the blood sample. In this example, while conventionally detecting platelets, the alarming for a platelet aggregation sample is realized by controlling the reaction conditions for preparing the first test sample and the second test sample, and a new platelet aggregation alarm function is thus provided on the basis of the original sample preparation device and sample testing device of the blood cell analyzer. Therefore, suspected platelet aggregation samples can be screened out quickly and simply without increasing measurement complexity and costs.

Figure 6:
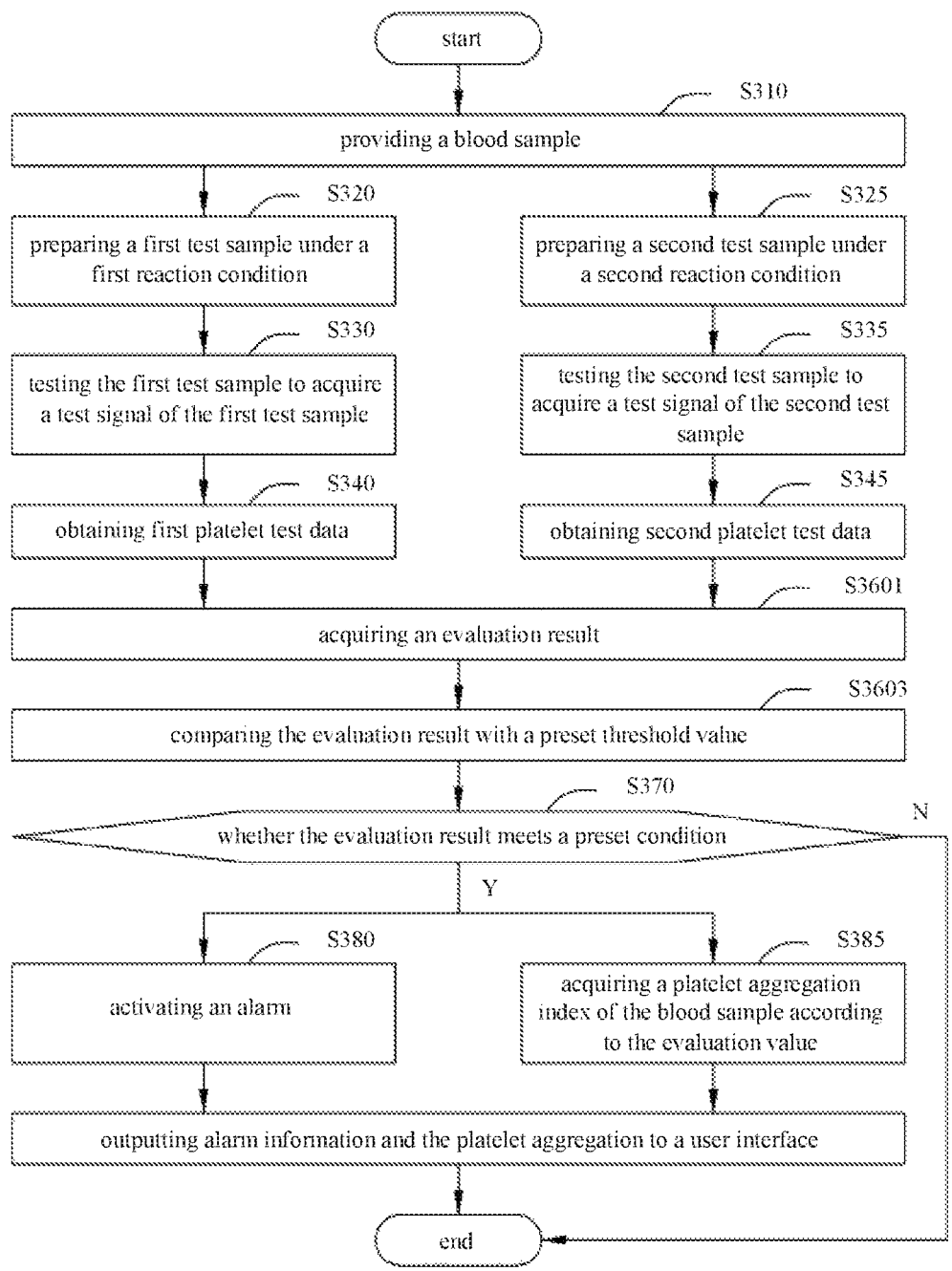
FIG. 6 is a flowchart of an alarming method for a platelet aggregation sample provided in a third embodiment of the present disclosure.

FIG. 6 shows a flowchart of an alarming method for a platelet aggregation sample provided in a third embodiment of the present disclosure. In step S3601, an evaluation value EV is calculated based on the obtained first platelet test data and second platelet test data. In step S2603, the numerical magnitudes of the evaluation value EV and a preset threshold value are compared with each other to obtain an evaluation result. The contents of steps S310-S3603 are basically the same as steps S110-S160 and S2101-2603 in the alarming method for a platelet aggregation sample provided in the previous embodiments, and will not be described further here.

In the third embodiment, in step S370, it is determined whether the evaluation result obtained in step S3603 meets a preset condition. When the determination result is YES, an alarm is given in step S380, and a platelet aggregation index of the blood sample is acquired in step S385. Then, in step S390, the alarm that the blood sample may be a platelet aggregation sample and the platelet aggregation index of the blood sample are output to the user interface. Alternatively, in step S390, only the platelet aggregation index of the blood sample may be output to the user interface.

Specifically, in step S385, the controller 70 obtains the platelet aggregation index of the blood sample based on the evaluation value obtained in step S3601 according to a correlation between a set of preset evaluation values EV and platelet aggregation indexes IN. It can be understood that the correlation between the preset evaluation values EV and the platelet aggregation indexes IN can be stored in advance in the memory 83 of the blood cell analyzer 1. The evaluation value EV is used to quantitatively reflect the degree of difference between the first platelet test data and the second platelet test data, and the platelet aggregation index IN is used to qualitatively explain the platelet aggregation degree in a blood sample. Optionally, the higher the platelet aggregation index IN is, the higher the platelet aggregation degree in the blood sample is. It can be understood that the platelet aggregation index IN can also be correlated with the evaluation value EV in the form of letters or written descriptions.

It can be understood that the preset EV-IN correlation is obtained from statistical empirical values. The correlation between the numerical range of the evaluation value EV and the platelet aggregation index IN is obtained through automated analysis and manual microscopic examination of hundreds to thousands of normal blood samples and platelet aggregation samples with different aggregation degrees. In one example, the platelet aggregation index IN may include 1—slight aggregation, 2—moderate aggregation, and 3—severe aggregation. Each platelet aggregation index IN corresponds to a numerical range of the evaluation value EV. When the evaluation value EV is positively correlated with the platelet aggregation degree, the relatively lower evaluation value EV corresponds to the lower platelet aggregation index IN, such as 1 (slight aggregation); and accordingly, a higher evaluation value EV corresponds to a higher platelet aggregation index IN, such as 3 (severe aggregation). The preset EV-IN correlation is stored in the memory 83 of the controller 70 in advance, so that the controller 70 can obtain the platelet aggregation index IN of the blood sample in step S385 according to the evaluation value EV of the test blood sample and the preset EV-IN correlation and output the result to the user interface 90.

Further, the controller 70 can also determine whether to start the retest process according to the value of the obtained platelet aggregation index IN of the blood sample. For instance, in the example of the above paragraph, when IN=3, the controller 70 sends a signal to another blood cell analyzer or a smearing and staining machine to retest the blood sample. It should be noted that the third embodiment of the present disclosure is not limited by the above example, and the above example is only used to explain the method provided in the third embodiment.

The third embodiment not only provides a platelet aggregation sample alarm function for the blood cell analyzer, but also further qualitatively evaluates the platelet aggregation degree of the corresponding blood sample, which is convenient for the user to determine the subsequent analysis and test scheme of the corresponding blood sample according to the platelet aggregation index IN.

Figure 7:
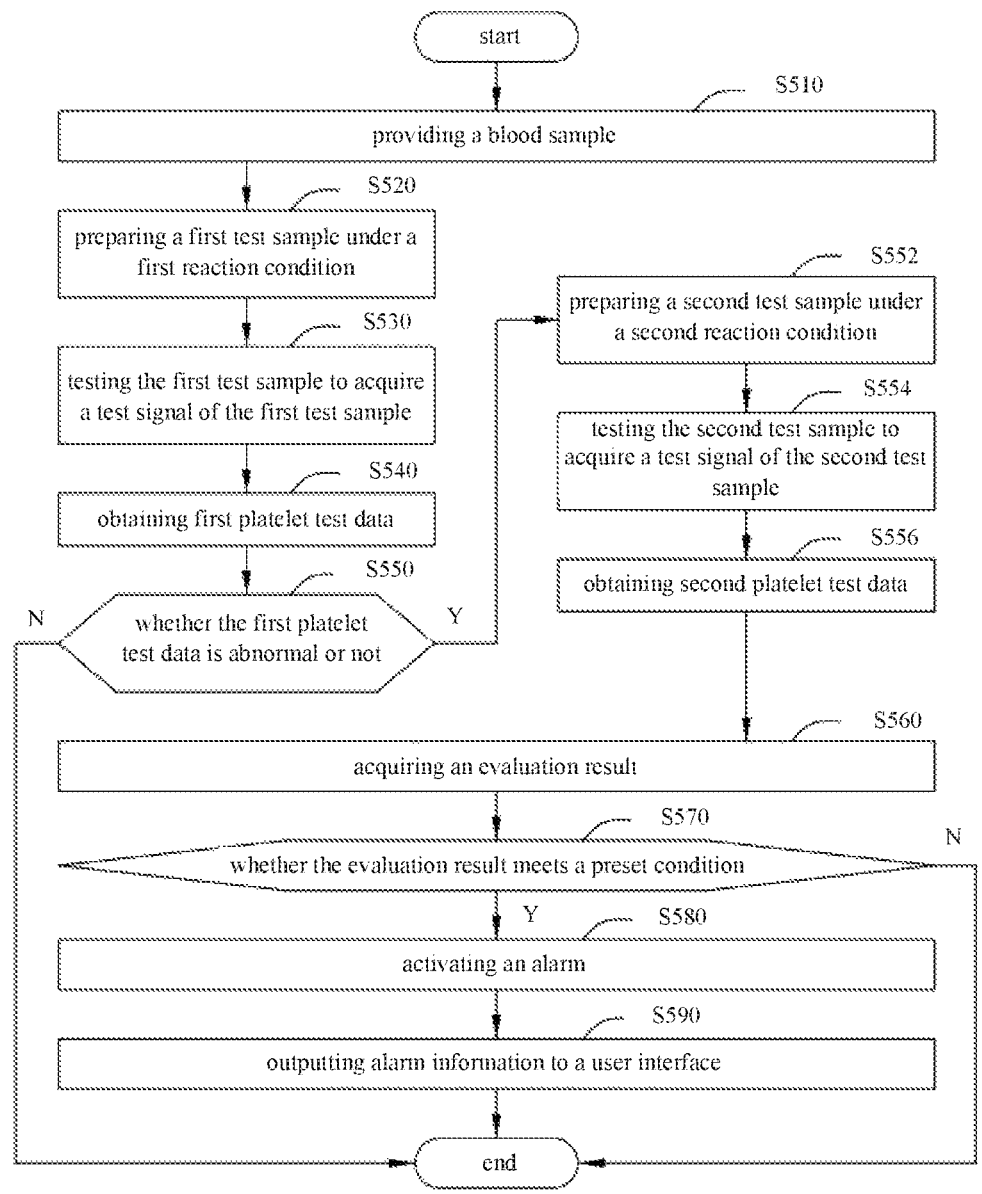
FIG. 7 is a flowchart of an alarming method for a platelet aggregation sample provided in a fourth embodiment of the present disclosure.

FIG. 7 shows a flowchart of an alarming method for a platelet aggregation sample provided in a fourth embodiment of the present disclosure, comprising:

step S510 of providing a blood sample;

step S520 of preparing a first test sample from the blood sample under a first reaction condition;

step S530 of testing the first test sample to acquire a test signal of the first test sample;

step S540 of obtaining first platelet test data according to the test signal of the first test sample;

step S550 of determining whether the first platelet test data is abnormal or not;

step S552 of preparing a second test sample from the blood sample under a second reaction condition when the determination result in step S550 is YES, wherein compared with the first reaction condition, the second reaction condition can reduce the platelet aggregation degree in the blood sample;

step S554 of testing the second test sample to acquire a test signal of the second test sample;

step S556 of obtaining second platelet test data according to the test signal of the second test sample;

step S560 of acquiring an evaluation result based on the first platelet test data and the second platelet test data;

step S570 of determining whether the evaluation result meets a preset condition;

step S580 of activating an alarm when the determination result of step S570 is YES; and step S590 of outputting an alarm signal to a user interface.

Compared with the alarming method for a platelet aggregation sample provided in the second embodiment of the present disclosure, in the fourth embodiment, a blood sample is first prepared as a first test sample for test, and reliability determination is performed on the first platelet test data (e.g., the first platelet count PLT1). Specifically, in step S550, the analyzing and alarming unit 79 of the controller 70 determines whether there is abnormality in the first platelet test data, and when the determination result is YES, a second test sample is prepared and tested to determine whether the blood sample is a platelet aggregation sample. When the determination result is NO, the workflow ends and the method moves on to test the next blood sample.

Specifically, in one example, the first platelet test data is a first platelet count PLT1. The first platelet count value PLT1 may be obtained by testing via the electrical impedance testing component 51 of the blood cell analyzer or may be obtained by testing via the optical testing component 53. In step S550, it is determined whether the first platelet count PLT1 is less than a preset threshold value, that is, whether the platelet count of the first test sample is too low. Steps S552-S590 are executed when the determination result is YES. When the determination result is NO, the test process of the blood sample ends and the method moves on to test the next blood sample. It can be understood that the preset threshold value for determining whether the first platelet count PLT1 is abnormal comes from statistical empirical values. It can be understood that the step of determining whether the first platelet test data is abnormal can also be realized by comparing the numerical magnitudes of another type of platelet test data and a preset threshold value.

In steps S552-S590, a second test sample is prepared under a second reaction condition capable of reducing platelet aggregation degree, second platelet test data is acquired, an evaluation result is acquired based on the first and second platelet test data, whether the obtained evaluation result meets a preset condition is determined, and when the determination result is YES, an alarm is activated and the alarm information is output to the user interface. The specific contents of these steps are basically similar to those disclosed in the aforementioned second embodiment and will not be further described here.

It can be understood that, when the blood processing reagents used for preparing the first test sample and the second test sample are the same, and the sample testing parts for detecting the first test sample and the second test sample are also the same, in an example of the fourth embodiment, when it is determined in step S550 that the first platelet test data is abnormal, the tested first sample is conveyed back to the sample processing device by the liquid path system of the blood cell analyzer, and the second test sample is prepared from the tested first sample under the second reaction condition in step S552, and then steps S554-S590 are performed. Similarly, in the second embodiment provided by the present disclosure, after the test of the first test sample is completed, the first test sample can be conveyed to the sample processing device through the liquid path system to be prepared into the second test sample under the second reaction condition for subsequent test, calculation, determination and other steps.

Those skilled in the art can understand that in the workflow of the alarming method for a platelet aggregation sample disclosed in the second embodiment of the present disclosure, the step of determining whether there is abnormality in the first platelet test data can also be provided in addition. For example, after obtaining the first platelet test data in step S140, it is determined whether there is abnormality in the first platelet test data. When the determination result is YES (that is, there is abnormality), step S160 is executed to obtain the evaluation result; and when the determination result is NO, the workflow ends and the method moves on to test the next blood sample.

Further, the step of acquiring and outputting the platelet aggregation index IN disclosed in the third embodiment of the present disclosure can also be applied to steps S580-S590 in the fourth embodiment, and will not be described further here.

In order to better illustrate the alarming method for a platelet aggregation sample disclosed by the present disclosure, several examples are given below.

Example I

Figure 8A:
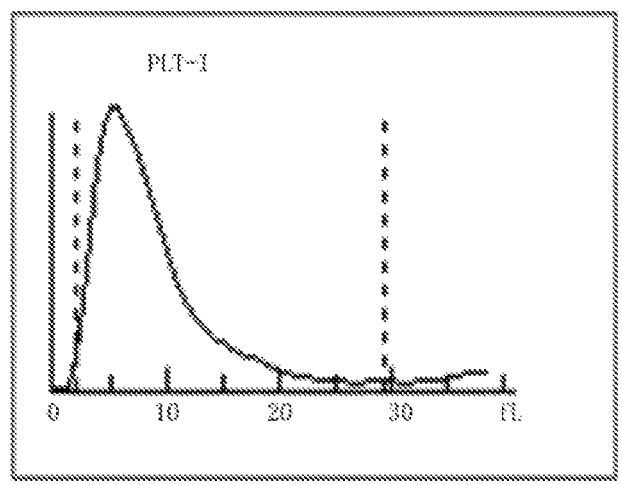
FIGS. 8A and 8B are a histogram of a first test sample and a forward scattered light-fluorescence scatterdiagram of a second test sample, the first test sample and the second test sample are respectively obtained when blood sample A is tested by a method provided by certain embodiments of the present disclosure.
Figure 8B:
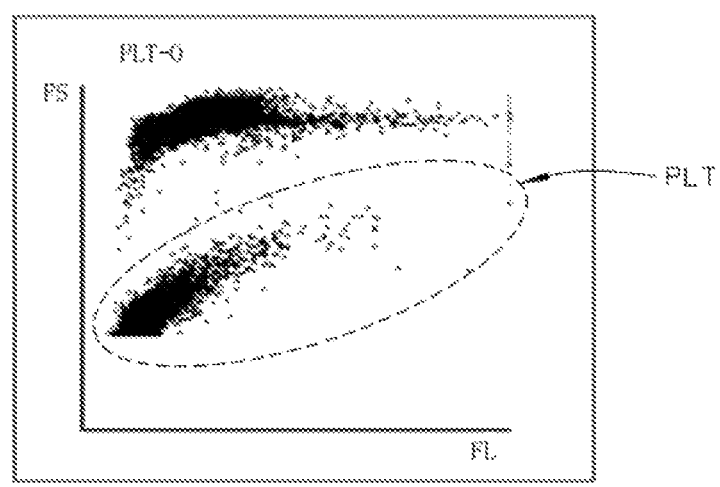

Blood sample A was tested using a method disclosed in an example of the second embodiment of the present application (FIG. 5). Specifically, in step S220, the first reaction condition was controlled to include a temperature of 25 degrees Celsius and bubble mixing, and in step S225, the second reaction condition was controlled to include a temperature of 42 degrees Celsius and agitator arm mixing (600 rpm). The histogram of the first test sample as shown in FIG. 8A is obtained in step S2401, and the first platelet count PLT1 obtained in step S2403 is $229*10^9/L$. Accordingly, in step S2451, the forward scattered light-fluorescence scatter-diagram of the second test sample as shown in FIG. 8B was obtained, and the second platelet count PLT2 obtained in step S2453 was $231*10^9/L$. In this example, the preset condition used is that $10^{-9}*(PLT2-PLT1)$ is greater than the preset threshold value of 30. For blood sample A, the evaluation value obtained by calculating $10^{-9}*(PLT2-PLT1)$ is 2, which is less than the preset threshold value of 30, so that the evaluation result does not meet the preset condition, and the workflow ends without alarming.

The blood sample A was tested by manual microscopic examination to confirm that the blood sample A is a non-platelet aggregation sample.

Example II

Figure 9A:
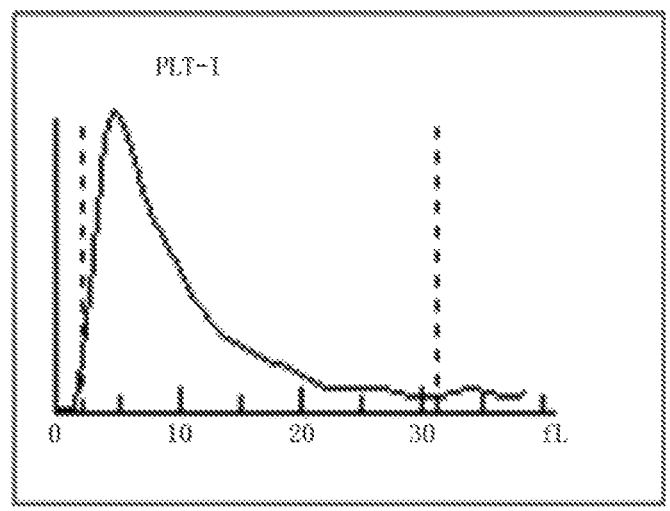
FIGS. 9A and 9B are a histogram of a first test sample and a forward scattered light-fluorescence scatterdiagram of a second test sample, the first test sample and the second test sample are respectively obtained when blood sample B is tested by a method provided by certain embodiments of the present disclosure.
Figure 9B:
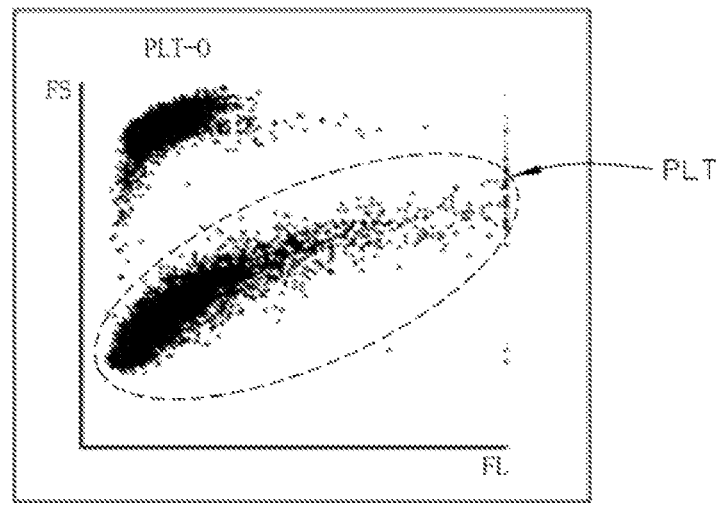

Blood sample B was tested using a method disclosed in an example of the second embodiment of the present application (FIG. 5). Specifically, in step S220, the first reaction condition was controlled to include a temperature of 25 degrees Celsius and bubble mixing, and in step S225, the second reaction condition was controlled to include a temperature of 42 degrees Celsius and agitator arm mixing (600 rpm). The histogram of the first test sample as shown in FIG. 9A was obtained in step S2401, and the first platelet count PLT1 obtained in step S2403 was $197*10^9/L$. Accordingly, in step S2451, the forward scattered light-fluorescence scatterdiagram of the second test sample as shown in FIG. 9B was obtained, and the second platelet count PLT2 obtained in step S2453 was $436*10^9/L$. In this example, the preset condition used is that $10^{-9}*(PLT2-PLT1)$ is greater than the preset threshold value of 30. For blood sample B, the evaluation value obtained by calculating $10^{-9}*(PLT2-PLT1)$ is 239, which is greater than the preset threshold value of 30, so that the evaluation result meets the preset condition and an alarm is activated to prompt that blood sample B may be a platelet aggregation sample.

The blood sample B was tested by manual microscopic examination to confirm that the blood sample B is a platelet aggregation sample.

Example III

Figure 10A:
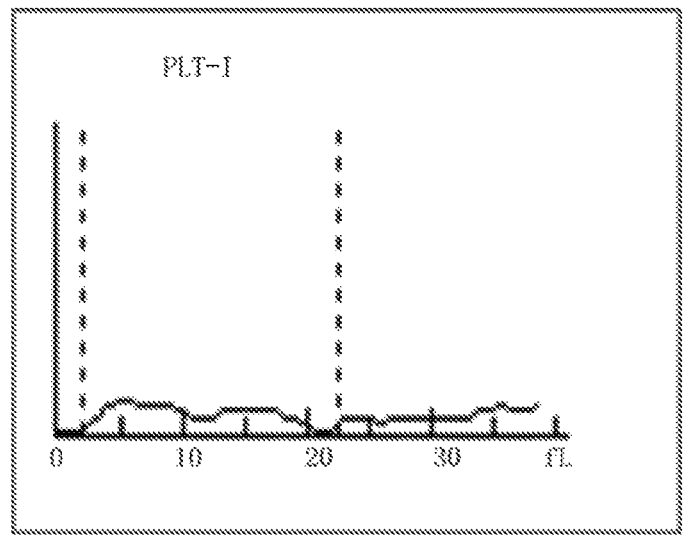
FIGS. 10A and 10B are a histogram of a first test sample and a forward scattered light-fluorescence scatterdiagram of a second test sample, the first test sample and the second test sample are respectively obtained when blood sample C is tested by a method provided by certain embodiments of the present disclosure.
Figure 10B:
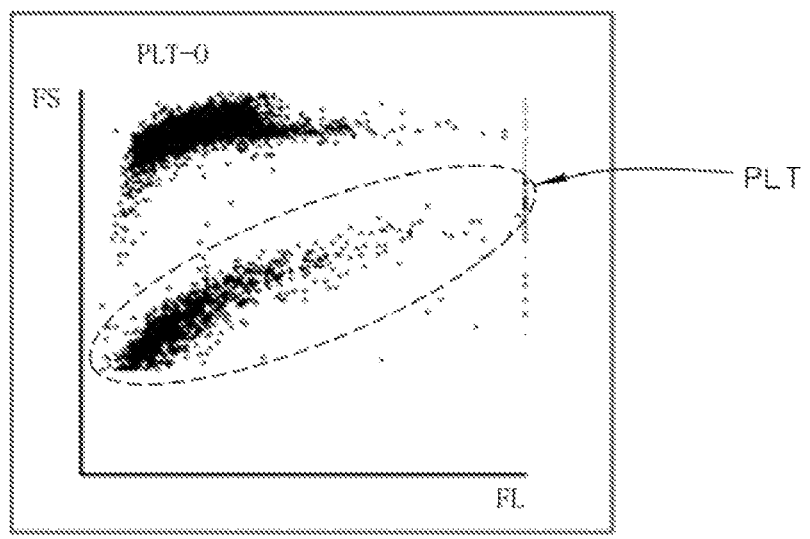

Blood sample C was tested using a method disclosed in the fourth embodiment of the present application (FIG. 7). Specifically, in step S520, a first test sample was prepared under the first reaction condition which was controlled to include a temperature of 25 degrees Celsius, adding diluent and bubble mixing. The electrical impedance signals of the first test sample were detected in step S530, and the histogram of the first test sample as shown in FIG. 10A was obtained based on the obtained electrical impedance signals in step S540, so that the first platelet test data PLT1 obtained was $7*10^9$/L. In Step S550, it was determined that the value of PLT1 was abnormal, and step S552 was executed to perform spheroidization and fluorescence staining on the blood sample under the second reaction condition controlled to include a temperature of 42 degrees Celsius and agitator arm mixing (600 rpm). In step S530, forward scattered light and fluorescence signals of the second test sample were detected, and in step S556, a forward scattered light-fluorescence scatterdiagram of the second test sample as shown in FIG. 10B was obtained, and the second platelet test data PLT2 obtained was $61*10^9$/L. In this example, the preset condition used is that PLT2/PLT1 is greater than the preset threshold value of 1.3. For blood sample C, the evaluation result calculated based on the PLT1 and the PLT2 is PLT2/PLT1=8.7, which is greater than the preset threshold value of 1.3, so that the evaluation result meets the preset condition, and an alarm is activated to prompt that blood sample C may be a platelet aggregation sample.

The blood sample C was tested by manual microscopic examination to confirm that the blood sample C is a platelet aggregation sample.

Example IV

Figure 11A:
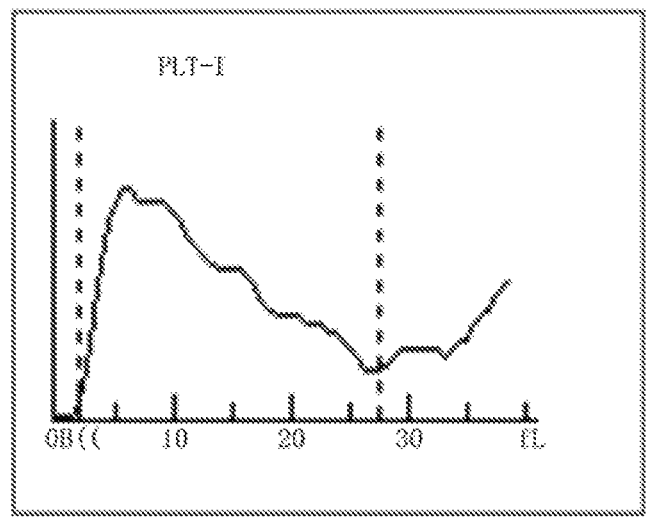
FIGS. 11A and 11B are a histogram of a first test sample and a forward scattered light-fluorescence scatterdiagram of a second test sample, the first test sample and the second test sample are respectively obtained when blood sample D is tested by a method provided by certain embodiments of the present disclosure.
Figure 11B:
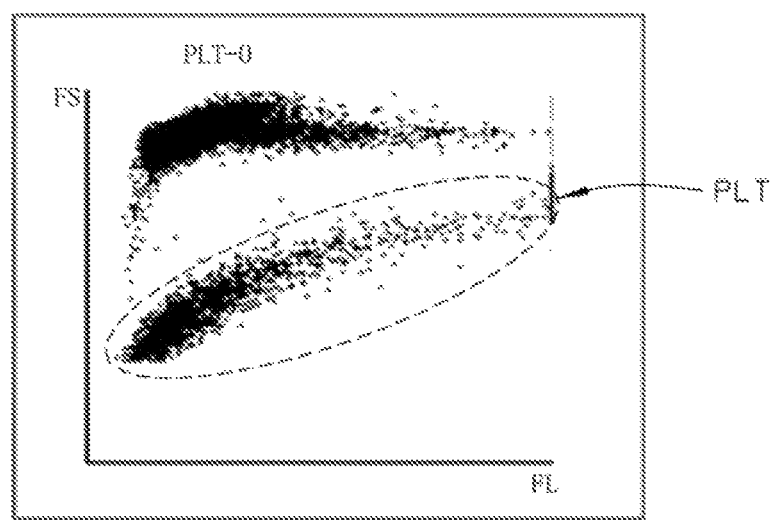

Blood sample D was tested using a method disclosed in an example of the second embodiment of the present application (FIG. 5). Specifically, in step S220, the first reaction condition was controlled to include a temperature of 25 degrees Celsius and bubble mixing, and in step S225, the second reaction condition was controlled to include a temperature of 42 degrees Celsius and agitator arm mixing (600 rpm). The histogram of the first test sample as shown in FIG. 11A was obtained in step S2401, and the first platelet count PLT1 obtained in step S2403 was $45*10^9$/L. Accordingly, in step S2451, the forward scattered light-fluorescence scatterdiagram of the second test sample as shown in FIG. 11B was obtained, and the second platelet count PLT2 obtained in step S2453 was $94*10^9$/L. In this example, the preset condition used is that PLT2/PLT1 is greater than a preset threshold value of 1.25 and $10^{-9}*(PLT2-PLT1)$ is greater than another preset threshold value of 25. For blood sample D, based on PLT1 and PLT2, the evaluation result PLT2/PLT1=2.1 is greater than a preset threshold value of 1.25 and $10^{-9}*(PLT2-PLT1)=49$ is greater than the another preset threshold value of 25, so that the evaluation result meets the preset condition, and an alarm is activated to prompt that blood sample D may be a platelet aggregation sample.

The blood sample D was tested by manual microscopic examination to confirm that the blood sample D is a platelet aggregation sample.

Example V

Figure 12A:
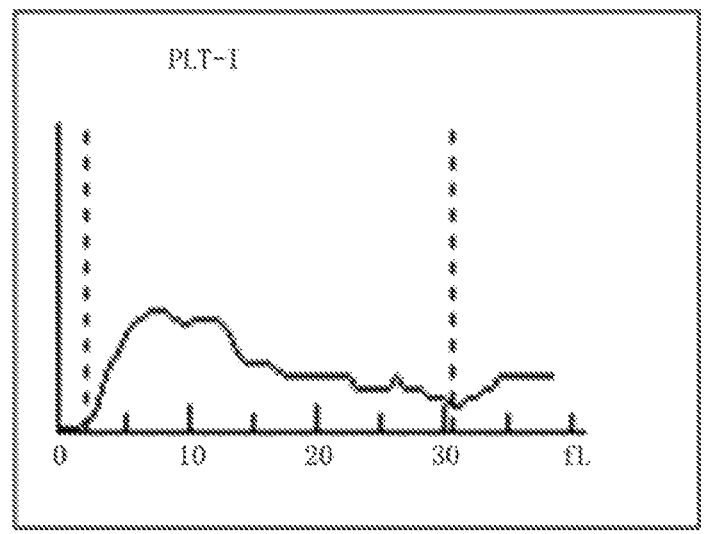
FIGS. 12A and 12B are a histogram of a first test sample and a histogram of a second test sample, the first test sample and the second test sample are respectively obtained when blood sample E is tested by a method provided by the present disclosure.

Blood sample E was tested using a method disclosed in the second embodiment of the present application (FIG. 4). Specifically, in step S120, the first reaction condition was controlled to include bubble mixing with low mixing intensity after diluent is added to prepare a first test sample. Correspondingly, in step S125, the second reaction condition was controlled to include agitator arm mixing with high mixing intensity after diluent is added to prepare a second test sample. The temperatures for preparing the first test sample and the second test sample were both 25 degrees Celsius. In steps S130 and S135, the electrical impedance testing component was used to detect electrical impedance signals of the first and second test samples, respectively. In step S140, the histogram of the first test sample as shown in FIG. 12A was obtained, and the first platelet test data PLT1 obtained was $24*10^9$/L. In step S145, the histogram of the second test sample as shown in FIG. 12B was obtained, and the second platelet test data PLT2 obtained was $132*10^9$/L.

When the preset condition used is that $10^{-9}*(PLT1-PLT2)$ is less than a preset threshold value of −30, for blood sample E, the evaluation result based on the PLT1 and the PLT2 is $10^{-9}*(PLT1-PLT2)=-108$, which is less than the preset threshold value of −30, so that the evaluation result meets the preset condition, and an alarm is activated to prompt that blood sample E may be a platelet aggregation sample.

When the preset condition used is that PLT1/PLT2 is less than a preset threshold value of 0.77, for blood sample E, the evaluation result based on the PLT1 and PLT2 is PLT1/PLT2=0.18, which is less than the preset threshold value of 0.77, so that the evaluation result meets the preset condition, and an alarm is activated to prompt that blood sample E may be a platelet aggregation sample.

Figure 12B:
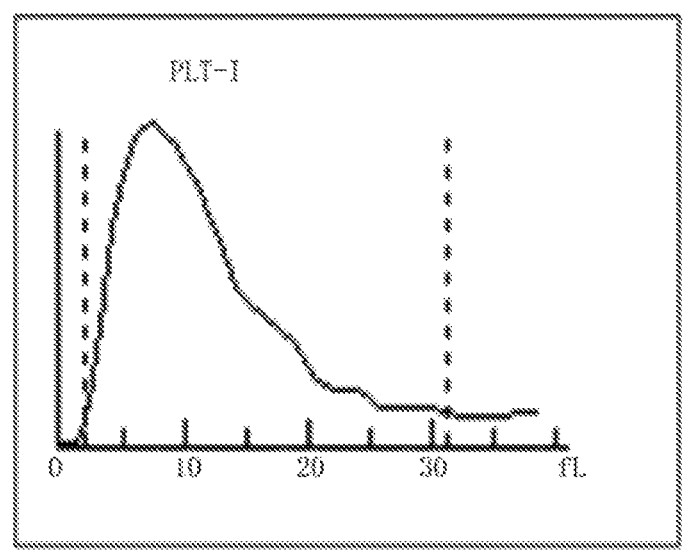

In addition, when the preset condition used is that the graph of the second platelet test data is not similar to the graph of the first platelet test data, the two graphs reflecting the first and second platelet test data shown in FIGS. 12A and 12B can be compared in the same cell volume interval (i.e., the same abscissa interval), by a graph comparison technique to obtain the evaluation result. For blood sample E, the evaluation result obtained through graph comparison is "not similar", so that the evaluation result meets the preset condition, and an alarm is activated to prompt that blood sample E may be a platelet aggregation sample.

The blood sample E was tested by manual microscopic examination to confirm that the blood sample E is a platelet aggregation sample.

Example VI

Figure 13A:
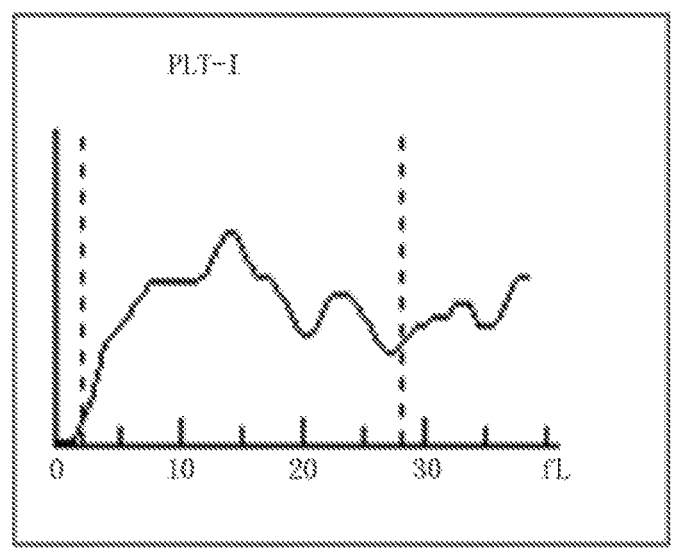
FIGS. 13A and 13B are a histogram of a first test sample and a histogram of a second test sample, the first test sample and the second test sample are respectively obtained when blood sample F is tested by a method provided by certain embodiments of the present disclosure.
Figure 13B:
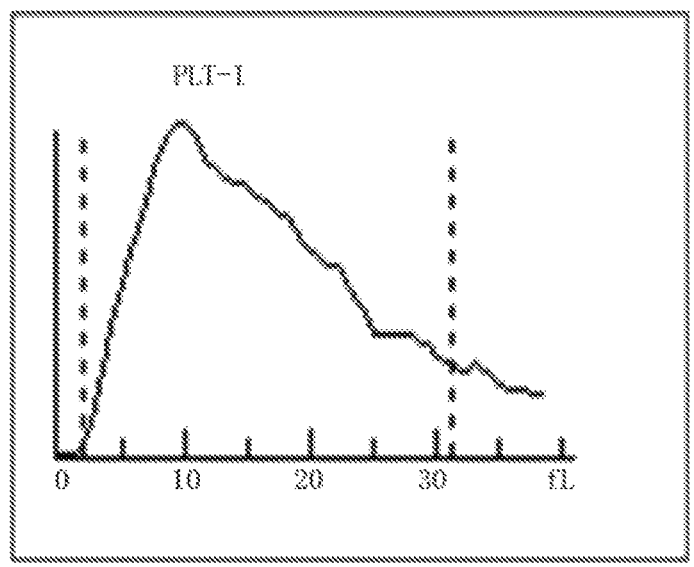

Blood sample F was tested using a method disclosed in the second embodiment of the present application (FIG. 4). Specifically, in step S120, a first test sample was prepared under the first reaction condition which was controlled to include a temperature of 25 degrees Celsius and mixing with diluent added. Correspondingly, in step S125, a second test sample was prepared under the second reaction condition which was controlled to include a temperature of 37 degrees Celsius and mixing with diluent added. The mixing methods for preparing the first test sample and the second test sample were both bubble mixing. In steps S130 and S135, electrical impedance signals of the first and second test samples were detected respectively by the electrical impedance testing component. In step S140, the histogram of the first test sample as shown in FIG. 13A was obtained, and the first platelet test data PLT1 obtained was $40*10^9$/L. In step S145, the histogram of the second test sample as shown in FIG. 13B was obtained, and the second platelet test data PLT2 obtained was $101*10^9$/L.

When the preset condition used is that $10^{-9}*(PLT2-PLT1)$ is greater than a preset threshold value of 30, for blood sample F, the evaluation result based on the PLT1 and the PLT2 is $10^{-9}*(PLT2-PLT1)=61$, which is greater than the preset threshold value of 30, so that the evaluation result meets the preset condition, and an alarm is activated to prompt that blood sample F may be a platelet aggregation sample.

When the preset condition used is that PLT1/PLT2 is less than a preset threshold value of 0.77, for blood sample F, the evaluation result based on the PLT1 and PLT2 is PLT1/PLT2=0.4, which is less than the preset threshold value of 0.77, so that the evaluation result meets the preset condition, and an alarm is activated to prompt that blood sample F may be a platelet aggregation sample.

The blood sample F was tested by manual microscopic examination to confirm that the blood sample F is a platelet aggregation sample.

Example VII

Figure 14A:
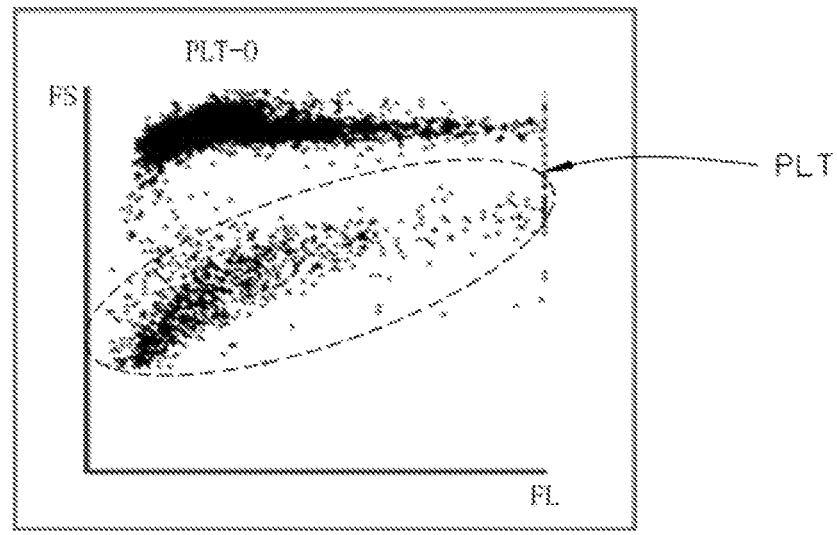
FIGS. 14A and 14B are a forward scattered light-fluorescence scatterdiagram of a first test sample and a forward scattered light-fluorescence scatterdiagram of a second test sample, the first test sample and the second test sample are respectively obtained when blood sample G is tested by a method provided by certain embodiments of the present disclosure.
Figure 14B:
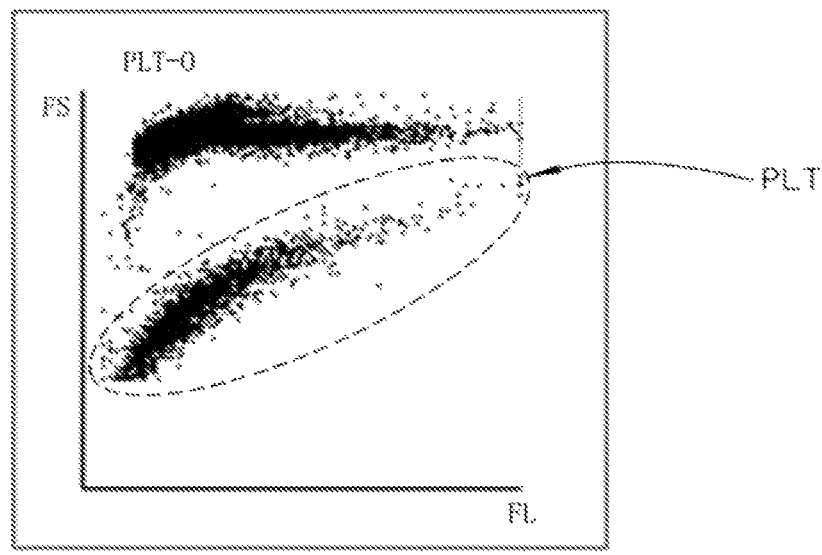

Blood sample G was tested using a method disclosed in the second embodiment of the present application (FIG. 4). Specifically, in step S120, the first reaction condition was controlled to include mixing with a low mixing intensity and with an agitation speed of 600 rpm, and the blood sample was subjected to spheroidization and fluorescence staining to obtain a first test sample. Correspondingly, in step S125, the second reaction condition was controlled to include mixing with a high mixing intensity and with an agitation speed of 1400 rpm, and the blood sample was subjected to spheroidization and fluorescence staining to obtain a second test sample. The temperatures for preparing the first test sample and the second test sample were both 42 degrees Celsius. In steps S130 and S135, forward scattered light signals and fluorescence signals of the first and second test samples were respectively detected by the optical testing component. In step S140, the forward scattered light-fluorescence scatterdiagram of the first test sample as shown in FIG. 14A was obtained, and the first platelet test data PLT1 obtained was $51*10^9$/L. In step S145, the forward scattered light-fluorescence scatterdiagram of the second test sample as shown in FIG. 14B was obtained, and the second platelet test data PLT2 obtained was $100*10^9$/L.

When the preset condition used is that (PLT2−PLT1)/PLT1 is greater than a preset threshold value of 0.3, for blood sample G, the evaluation result based on the PLT1 and PLT2 is (PLT2−PLT1)/PLT1=0.96, which is greater than the preset threshold value of 0.3, so that the evaluation result meets the preset condition, and an alarm is activated to prompt that blood sample G may be a platelet aggregation sample.

When the preset condition used is that $10^{-9}*$(PLT2−PLT1) is greater than a preset threshold value of 30, for blood sample G, the evaluation result based on the PLT1 and the PLT2 is $10^{-9}*$(PLT2−PLT1)=49, which is greater than the preset threshold value 30, so that the evaluation result meets the preset condition, and an alarm is activated to prompt that blood sample G may be a platelet aggregation sample.

The blood sample G was tested by manual microscopic examination to confirm that the blood sample G is a platelet aggregation sample.

Example VIII

Figure 15A:
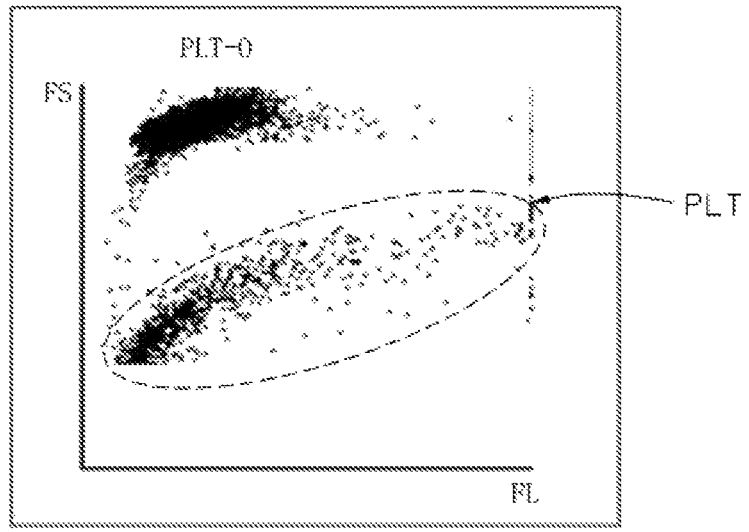
FIGS. 15A and 15B are a forward scattered light-fluorescence scatterdiagram of a first test sample and a forward scattered light-fluorescence scatterdiagram of a second test sample, the first test sample and the second test sample are respectively obtained when blood sample H is tested by a method provided by certain embodiments of the present disclosure.
Figure 15B:
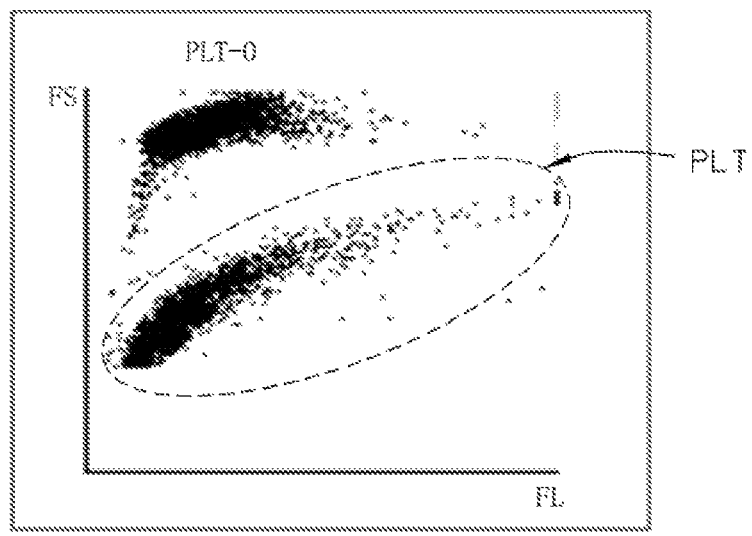

Blood sample H was tested using a method disclosed in the second embodiment of the present application (FIG. 4). Specifically, in step S120, the first reaction condition was controlled to include bubble mixing, and the blood sample was subjected to spheroidization and fluorescence staining to obtain a first test sample. Correspondingly, in step S125, the second reaction condition was controlled to include agitator arm mixing (600 rpm), and the blood sample was subjected to spheroidization and fluorescence staining to obtain a second test sample. The temperatures for preparing the first test sample and the second test sample were both 42 degrees Celsius. In steps S130 and S135, forward scattered light signals and fluorescence signals of the first and second test samples were detected respectively by the optical testing component. In step S140, the forward scattered light-fluorescence scatterdiagram of the first test sample as shown in FIG. 15A was obtained, and the first platelet test data PLT1 obtained was $46*10^9$/L. In step S145, the forward scattered light-fluorescence scatterdiagram of the second test sample as shown in FIG. 15B was obtained, and the second platelet test data PLT2 obtained was $117*10^9$/L.

When the preset condition used is that (PLT2−PLT1)/PLT1 is greater than a preset threshold value of 0.3, for blood sample H, the evaluation result based on the PLT1 and PLT2 is (PLT2−PLT1)/PLT1=1.54, which is greater than the preset threshold value of 0.3, so that the evaluation result meets the preset condition, and an alarm is activated to prompt that blood sample H may be a platelet aggregation sample.

When the preset condition used is that $10^{-9}*$(PLT2−PLT1) is greater than a preset threshold value of 30, for blood sample H, the evaluation result based on the PLT1 and the PLT2 is $10^{-9}*$(PLT2−PLT1)=71, which is greater than the preset threshold value 30, so that the evaluation result meets the preset condition, and an alarm is activated to prompt that blood sample H may be a platelet aggregation sample.

The blood sample H was tested by manual microscopic examination to confirm that the blood sample H is a platelet aggregation sample.

Example IX

Blood sample H was tested using a method disclosed in the second embodiment of the present application (FIG. 4). Specifically, in step S120, the first reaction condition was controlled to include bubble mixing, and the blood sample was subjected to spheroidization and fluorescence staining to obtain a first test sample. Correspondingly, in step S125, the second reaction condition was controlled to include agitator arm mixing (600 rpm), and the blood sample was subjected to spheroidization and fluorescence staining to obtain a second test sample. The temperatures for preparing the first test sample and the second test sample were both 42 degrees Celsius. In steps S130 and S135, forward scattered light signals, side scattered light signals, and fluorescence signals of the first and second test samples were detected respectively by the optical testing component. In step S140, the forward scattered light-fluorescence scatterdiagram of the first test sample as shown in FIG. 15A was obtained, and in step S145, the forward scattered light-fluorescence scatterdiagram of the second test sample as shown in FIG. 15B was obtained. The classifying and counting unit 77 distinguishes the platelet region based on the forward scattered light-fluorescence scatterdiagram of the first and second test samples, and then calculates the volume information of each platelet particle based on the forward scattered light (FS) and the side scattered light (SSC) of the particles in the platelet region by Tycko's method (for the specific method, refer to U.S. Pat. No. 4,735,504, the disclosure of which is incorporated herein by reference in its entirety). The classifying and counting unit 77 obtains optical PLT volume distribution histograms of the first and second test samples using the calculated platelet volume information.

Figure 16:
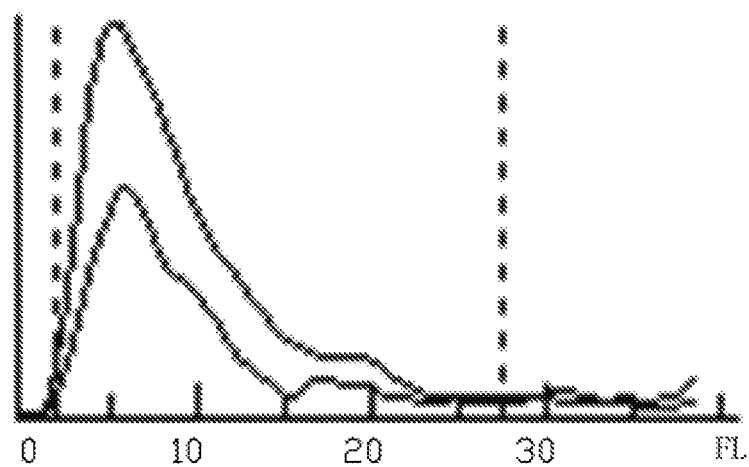
FIG. 16 is a graph comparison diagram of optical PLT volume distribution histograms of a first test sample and a second test sample obtained when blood sample H is tested by a method provided by certain embodiments of the present disclosure.

When the preset condition used is that the graph of the second platelet test data is not similar to the graph of the first platelet test data, the similarity degree of the optical PLT volume distribution histograms of the first and second test samples of the blood sample H in the same cell volume interval can be compared through the graph comparison technique to obtain the evaluation result, as shown in FIG. 16. For blood sample H, the evaluation result obtained through graph comparison is "not similar", so that the evaluation result meets the preset condition, and an alarm is activated to prompt that blood sample H may be a platelet aggregation sample.

The blood sample H was tested by manual microscopic examination to confirm that the blood sample H is a platelet aggregation sample.

The automatic tests of blood samples in the above examples were all performed by a blood cell analyzer BC-6800 manufactured by Shenzhen Mindray Bio-Medical Electronics Co., Ltd. The results of the above examples show that the detection of platelet aggregation samples by the method provided by the present disclosure has diversified execution modes and a high accuracy for alarming.

The alarming method for a platelet aggregation sample and a blood analyzer having this function provided by the present disclosure are described above by giving examples. Those skilled in the art can understand that all or part of the steps in the alarming method for a platelet aggregation sample can also be implemented by a computer program to instruct relevant hardware of a blood cell analyzer. The computer program can be stored in a computer readable storage medium and loaded into a blood cell analyzer having a corresponding hardware system. When a processor runs the computer program, the blood cell analyzer executes the alarming method for a platelet aggregation sample disclosed by the present disclosure.

If the platelet alarming method is implemented in the form of a software functional unit and sold or used as an independent product, it can be stored in a computer readable storage medium. Based on this interpretation, the present disclosure can also implement all or part of the workflow in the above-mentioned embodiments by a computer program to instruct relevant hardware. The computer program may be stored in a computer readable storage medium, and when executed by a processor, the computer program may implement the steps of the method examples above. The computer program can be loaded into a blood cell analyzer with a corresponding hardware system, and when the computer program is executed by a processor, the blood cell analyzer can execute the alarming method for a platelet aggregation sample disclosed by the present disclosure.

The computer program comprises computer program code, which may be in the form of source code, object code, an executable file or some intermediate form, etc. The computer readable medium may include any entity or device capable of carrying the computer program code, such as a recording medium, a USB flash drive, a mobile hard disk drive, a magnetic disk, a compact disk, computer memory, read-only memory (ROM), random access memory (RAM), an electrical carrier signal, a telecommunication signal and a software distribution medium.

In several embodiments provided by the present disclosure, it should be understood that the disclosed blood cell analyzer and alarming method for platelet aggregation can be realized by other means. The above-described embodiments are only schematic, in which the division of some functional units is only a kind of logical function division, and there may be other division modes in actual implementation.

The present disclosure, in various embodiments, also provides a nonvolatile computer-readable storage medium having stored thereon computer readable instructions which, when executed by a processor, perform the steps of any of the alarming method for a platelet aggregation sample of the second, third and fourth embodiments described above. The specific procedures and contents of each step can be referred to above and will not be described in detail here.

In the above description of various embodiments of the present invention, various functional units are described. These functional units may be variously implemented, for example, by hardware, software, or a combination thereof. For example, a hardware computer processor, such as a central processing unit (CPU), graphics processing unit (GPU), or the like, having one or many processing cores, and capable of handling one or many simultaneous threads, may be configured with random access memory (RAM) and/or read-only memory (ROM) to carry out the functions. A single hardware device may serve as multiple functional units. Alternatively, each functional unit may be its own separate hardware device. Where performance of a function involves the use of memory, the memory may be on a same chip or a different chip from the processor. Other storage, such as a single hard drive or array of drives, may be used to store data for the functional units. The functional units may be implemented using a single computer or using distributed computing or cloud computing. Other options are also permitted.

According to the alarming method for platelet aggregation, the blood cell analyzer and the nonvolatile computer-readable storage medium provided by certain embodiments of the present disclosure, two test samples prepared from the same blood sample are subjected to differentiated processing by controlling relevant structures and functional units of a sample processing device, and the differentiated processing can reduce the platelet aggregation degree in the blood sample. Through the differentiated blood sample processing methods, platelet-related test data of two test samples prepared from a platelet aggregation sample are obviously different from each other, while platelet-related test data of two test samples prepared from a non-platelet aggregation sample are relatively similar to each other. Therefore, it can be determined whether a blood sample is a platelet aggregation sample by comparing the platelet test data of two test sample. When the determination result is YES, an alarm for the platelet aggregation sample is activated.

On the basis of existing blood cell analyzers, certain embodiments of the present disclosure realize automatic alarming for platelet aggregation samples and lightens the workload of testing personnel by differentially controlling parameters such as temperature, mixing intensity, concentration of blood processing reagents, reacting time between blood processing reagents and blood samples in the preparation of the first and second test samples from the same blood sample and designing the analyzing and processing workflow of test results. Meanwhile, the platelet aggregation alarming method disclosed by certain embodiments of the present disclosure can be applied to hardware systems of the existing blood cell analyzers, thus controlling the manufacturing costs of the blood cell analyzers while providing a new test function for the blood cell analyzers. In addition, based on various embodiments of the present disclosure, only one sample processing part and one sample testing part are required in order to realize alarming for a platelet aggregation sample, which is beneficial to miniaturization of the blood cell analyzer.

The technical features or execution steps described in embodiments of the present disclosure may be implemented or combined in any suitable manner. The steps or sequences of the methods described herein can be changed without departing from the scope and broadly understood description of the present disclosure. The sequences described in detail in the drawings and various examples are only for better explanation of the present disclosure and are not used to limit the scope of protection of the present disclosure. Any changes or substitutions that can easily occur to those skilled in the art within the scope of the present disclosure are included within the scope of protection of the present disclosure.

The invention claimed is:

1. An alarming method for a platelet aggregation sample, comprising:
    providing a blood sample;
    preparing a first test sample from the blood sample under a first reaction condition;
    acquiring a test signal of the first test sample to obtain first platelet test data;
    preparing a second test sample from the blood sample under a second reaction condition;
    acquiring a test signal of the second test sample to obtain second platelet test data, wherein the test signal of the first test sample and the test signal of the second test sample are respectively selected from at least one of an electrical impedance signal, a scattered light signal or a fluorescence signal, and the first platelet test data and the second platelet test data comprise at least one of platelet count, mean platelet volume or platelet distribution width, respectively;
    comparing the first platelet test data with the second platelet test data; and
    determining that the blood sample may be a platelet aggregation sample based on a comparison result;
    wherein the first reaction condition is different from the second reaction condition, the second reaction condition comprises a reaction condition for reducing a platelet aggregation degree of the blood sample, and the first reaction condition and the second reaction condition comprise at least one of reaction temperature, mixing intensity, blood processing reagent concentration or blood processing reagent action time, respectively.

2. The alarming method of claim 1, wherein the first reaction condition differs from the second reaction condition by at least one of the reaction temperature, the mixing intensity, the blood processing reagent concentration or the blood processing reagent action time.

3. The alarming method of claim 2, wherein the first reaction condition comprises a reaction temperature that is not higher than 30 degrees Celsius, the second reaction condition comprises a reaction temperature that is not lower than 35 degrees Celsius, or the first reaction condition comprises a reaction temperature that is not higher than 30 degrees Celsius and the second reaction condition comprises a reaction temperature that is not lower than 35 degrees Celsius.

4. The alarming method of claim 2, wherein the first reaction condition comprises mixing by using bubbles, the second reaction condition comprises mixing by using an agitator arm, or the first reaction condition comprises mixing by using bubbles and the second reaction condition comprises mixing by using an agitator arm.

5. The alarming method of claim 1, wherein the test signal of the first test sample comprises an electrical impedance signal, and the test signal of the second test sample comprises a forward scattered light signal and a fluorescence signal.

6. The alarming method of claim 1, wherein the first platelet test data and the second platelet test data are both platelet count values.

7. The alarming method of claim 1, further comprising:
    outputting alarming information to a user interface prompting that the blood sample may be a platelet aggregation sample.

8. The alarming method of claim 1, wherein determining that the blood sample may be a platelet aggregation sample based on the comparison result comprises:
    acquiring an evaluation value by calculating the first platelet test data and the second platelet test data through a mathematical formula, the evaluation value reflecting a difference between the first platelet test data and the second platelet test data;
    comparing the evaluation value with a preset threshold value; and
    determining that the blood sample may be a platelet aggregation sample when the evaluation value meets the preset threshold value.

9. The alarming method of claim 8, further comprising:
    acquiring a platelet aggregation index of the blood sample based on the evaluation value according to a correlation between a set of preset evaluation values and platelet aggregation indexes; and
    outputting the acquired platelet aggregation index of the blood sample.

10. The alarming method of claim 1, wherein after the obtaining the first platelet test data and before the preparing the second test sample from the blood sample under the second reaction condition, the method further comprises:
    determining whether the first platelet test data is abnormal; and
    performing the preparing the second test sample from the blood sample under the second reaction condition, when the first platelet test data is abnormal.

11. A blood cell analyzer, comprising:
    a sample processing device for preparing a test sample from a blood sample;
    a sample testing device for detecting a test signal of the test sample;
    a controller, which comprises a control unit, a signal acquisition unit, a classifying and counting unit and an analyzing and alarming unit;
    wherein the control unit is configured to control the sample processing device to respectively prepare a first test sample from the blood sample under a first reaction condition and prepare a second test sample from the blood sample under a second reaction condition, wherein the first reaction condition is different from the second reaction condition, the second reaction condition comprises a reaction condition for reducing a platelet aggregation degree of the blood sample, and the first reaction condition and the second reaction condition comprise at least one of reaction temperature, mixing intensity, blood processing reagent concentration or blood processing reagent action time, respectively;

wherein the signal acquisition unit is configured to respectively acquire a test signal of the first test sample and a test signal of the second test sample detected by the sample testing device;

wherein the classifying and counting unit is configured to obtain first platelet test data according to the test signal of the first test sample, and obtain second platelet test data according to the test signal of the second test sample, the test signal of the first test sample and the test signal of the second test sample are respectively selected from at least one of an electrical impedance signal, a scattered light signal or a fluorescence signal, and the first platelet test data and the second platelet test data comprise at least one of platelet count, mean platelet volume or platelet distribution width, respectively; and wherein the analyzing and alarming unit is configured to compare the first platelet test data with the second platelet test data; and determine that the blood sample may be a platelet aggregation sample based on a comparison result.

12. The blood cell analyzer of claim 11, wherein the control unit is configured to control the first reaction condition to be different from the second reaction condition by at least one of the reaction temperature, the mixing intensity, the blood processing reagent concentration or the blood processing reagent action time.

13. The blood cell analyzer of claim 12, wherein the sample processing device comprises at least one reaction cell and a temperature control assembly for controlling a temperature of the at least one reaction cell, the at least one reaction cell is configured to respectively prepare the first test sample and the second test sample, the temperature control assembly is connected to the control unit, and the control unit is configured to control the reaction temperature included in the first reaction condition to be not higher than 30 degrees Celsius and the reaction temperature included in the second reaction condition to be not lower than 35 degrees Celsius, by controlling the temperature control assembly.

14. The blood cell analyzer of claim 12, wherein the sample processing device comprises a mixing assembly connected to the control unit, the mixing assembly comprises a bubble mixing part and an agitator arm mixing part, and the control unit is configured to control the bubble mixing part for mixing during preparing first test sample under the first reaction condition and control the agitator arm mixing part for mixing during preparing second test sample under the second reaction condition.

15. The blood cell analyzer of claim 11, wherein the sample testing device comprises an electrical impedance testing component which comprises a micro pore and two electrodes respectively arranged on two sides of the micro pore.

16. The blood cell analyzer of claim 11, wherein the sample testing device comprises an optical testing component which comprises a flow chamber, a light source and at least one light detector.

17. The blood cell analyzer of claim 11, wherein the first platelet test data and the second platelet test data obtained by the classifying and counting unit are both platelet count values.

18. The blood cell analyzer of claim 11, further comprising a user interface configured for receiving an alarm from the analyzing and alarming unit and prompting that the blood sample may be a platelet aggregation sample.

19. The blood cell analyzer of claim 11, wherein the analyzing and alarming unit is configured to obtain an evaluation value by calculating the first platelet test data and the second platelet test data through a mathematical formula, the evaluation value reflecting a difference between the first platelet test data and the second platelet test data; compare the evaluation value with a preset threshold value; and determine that the blood sample may be a platelet aggregation sample when the evaluation value meets the preset threshold value.

20. The blood cell analyzer of claim 19, wherein the analyzing and alarming unit is configured to acquire a platelet aggregation index of the blood sample according to a correlation between a set of preset evaluation values and platelet aggregation indexes and the evaluation value, and output the acquired platelet aggregation index of the blood sample to a user interface.

21. A nonvolatile computer-readable storage medium, comprising instructions stored thereon to implement an alarming method for a platelet aggregation sample when executed by a processor, wherein the alarming method comprises:

preparing a first test sample from a blood sample under a first reaction condition;

acquiring a test signal of the first test sample to obtain first platelet test data;

preparing a second test sample from the blood sample under a second reaction condition;

acquiring a test signal of the second test sample to obtain second platelet test data, wherein the test signal of the first test sample and the test signal of the second test sample are respectively selected from at least one of an electrical impedance signal, a scattered light signal or a fluorescence signal, and the first platelet test data and the second platelet test data comprise at least one of platelet count, mean platelet volume or platelet distribution width, respectively;

comparing the first platelet test data with the second platelet test data; and determining that the blood sample may be a platelet aggregation sample based on a comparison result;

wherein the first reaction condition is different from the second reaction condition, the second reaction condition comprises a reaction condition for reducing a platelet aggregation degree in the blood sample, and the first reaction condition and the second reaction condition comprise at least one of reaction temperature, mixing intensity, blood processing reagent concentration or blood processing reagent action time, respectively.

* * * * *